United States Patent
Boor et al.

(10) Patent No.: US 12,144,984 B2
(45) Date of Patent: Nov. 19, 2024

(54) DIAGNOSTIC CIRCUITRY FOR MONITORING AND MITIGATING ELECTROMAGNETIC INTERFERENCE (EMI) IN AN IMPLANTABLE PULSE GENERATOR

(71) Applicant: ADVANCED NEUROMODULATION SYSTEMS, INC., Plano, TX (US)

(72) Inventors: Steven Boor, Plano, TX (US); Daran DeShazo, Lewisville, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 1156 days.

(21) Appl. No.: 16/931,030

(22) Filed: Jul. 16, 2020

(65) Prior Publication Data

US 2021/0275805 A1    Sep. 9, 2021

Related U.S. Application Data

(60) Provisional application No. 62/984,607, filed on Mar. 3, 2020.

(51) Int. Cl.
| | |
|---|---|
| *A61N 1/08* | (2006.01) |
| *A61B 18/00* | (2006.01) |
| *A61M 31/00* | (2006.01) |
| *A61N 1/36* | (2006.01) |
| *A61N 1/362* | (2006.01) |

(Continued)

(52) U.S. Cl.
CPC .............. *A61N 1/086* (2017.08); *A61B 18/00* (2013.01); *A61N 1/36038* (2017.08); *A61N 1/36053* (2013.01); *A61N 1/36125* (2013.01); *A61N 1/36153* (2013.01); *A61N 1/3629* (2017.08); *A61N 1/3718* (2013.01); *A61N 1/39622* (2017.08); *A61N 2/002* (2013.01); *A61N 2/006* (2013.01); *H02M 3/07* (2013.01);

(Continued)

(58) Field of Classification Search
None
See application file for complete search history.

(56) References Cited

U.S. PATENT DOCUMENTS

| | | | | |
|---|---|---|---|---|
| 5,700,280 A | * | 12/1997 | Silvian | A61N 1/3925 607/5 |
| 5,745,350 A | * | 4/1998 | Archer | H02M 3/33507 363/80 |

(Continued)

OTHER PUBLICATIONS

Patent Cooperation Treaty, International Search Report and Written Opinion issued for PCT Application No. PCT/US2021/020685, dated Jul. 8, 2021, 15 pages.

*Primary Examiner* — Carl H Layno
*Assistant Examiner* — Manolis Pahakis
(74) *Attorney, Agent, or Firm* — Norton Rose Fulbright US LLP

(57) ABSTRACT

A system and method for measuring, monitoring and mitigating EMI interference in an implanted stimulation lead system associated with an IPG. A Kelvin connection scheme operative with a diagnostic circuit is provided for sensing an interference voltage induced at a Kelvin connect electrode of the lead system, wherein the diagnostic circuit is configured to generate one or more control signals for adjusting in substantially real time a common-mode voltage reference provided to supply a biasing voltage to the IPG circuitry.

8 Claims, 9 Drawing Sheets

(51) Int. Cl.
  *A61N 1/37* (2006.01)
  *A61N 1/39* (2006.01)
  *A61N 2/00* (2006.01)
  *H02M 3/07* (2006.01)
  *H03K 5/1252* (2006.01)
  *H03K 5/24* (2006.01)

(52) U.S. Cl.
  CPC ............ H03K 5/1252 (2013.01); H03K 5/24 (2013.01); *A61B 2018/00577* (2013.01); *A61M 31/002* (2013.01)

(56) References Cited

U.S. PATENT DOCUMENTS

| | | | | |
|---|---|---|---|---|
| 6,819,954 B2* | 11/2004 | Connelly | ........... | A61N 1/37512 607/27 |
| 8,160,717 B2* | 4/2012 | Ameri | ................. | A61N 1/3718 607/63 |
| 8,423,133 B2* | 4/2013 | Doerr | ....................... | A61N 1/37 607/2 |
| 8,554,300 B2* | 10/2013 | Doerr | ................... | A61N 1/3718 600/409 |
| 8,855,784 B2* | 10/2014 | Lyden | .................. | A61N 1/3956 607/63 |
| 11,351,376 B2* | 6/2022 | DeShazo | ........... | A61N 1/37241 |
| 2005/0197677 A1* | 9/2005 | Stevenson | ................ | H01G 4/35 607/36 |
| 2006/0293591 A1* | 12/2006 | Wahlstrand | .......... | A61N 1/3706 600/423 |
| 2008/0015641 A1* | 1/2008 | Armstrong | ......... | A61N 1/36153 607/2 |
| 2008/0132974 A1 | 6/2008 | Strother et al. | | |
| 2010/0312188 A1* | 12/2010 | Robertson | ........... | A61M 5/1723 600/300 |
| 2014/0236077 A1 | 8/2014 | Robertson et al. | | |
| 2015/0051670 A1 | 2/2015 | Hocken et al. | | |
| 2017/0143282 A1 | 5/2017 | Kovacs et al. | | |
| 2017/0259065 A1* | 9/2017 | Baru | .................. | A61N 1/36153 |
| 2018/0103908 A1* | 4/2018 | Balczewski | .......... | A61B 5/0031 |
| 2019/0134391 A1* | 5/2019 | Druke | .................. | A61N 1/0456 |
| 2019/0255333 A1* | 8/2019 | Baru | .................. | A61N 1/36153 |
| 2019/0336763 A1* | 11/2019 | Spurling | ............ | A61N 1/0456 |
| 2020/0025707 A1* | 1/2020 | Beaty | .................. | G01N 27/3274 |
| 2020/0155851 A1 | 5/2020 | Boor et al. | | |
| 2020/0268274 A1* | 8/2020 | Saliga | .................. | A61B 5/0537 |
| 2020/0306533 A1* | 10/2020 | DeShazo | ........... | A61N 1/36157 |
| 2020/0306543 A1* | 10/2020 | Boor | ........................ | H03K 5/02 |
| 2020/0306550 A1* | 10/2020 | DeShazo | .............. | A61B 5/4836 |
| 2020/0338352 A1* | 10/2020 | DeShazo | ................ | A61N 1/378 |
| 2020/0346005 A1* | 11/2020 | Boor | .................. | A61N 1/36157 |
| 2020/0346014 A1* | 11/2020 | Boor | .................. | A61N 1/36071 |
| 2020/0384274 A1* | 12/2020 | Boor | .................. | A61N 1/37211 |
| 2020/0406033 A1* | 12/2020 | Loh | .................. | A61N 1/36007 |
| 2021/0275805 A1* | 9/2021 | Boor | ........................ | H03K 5/24 |

\* cited by examiner

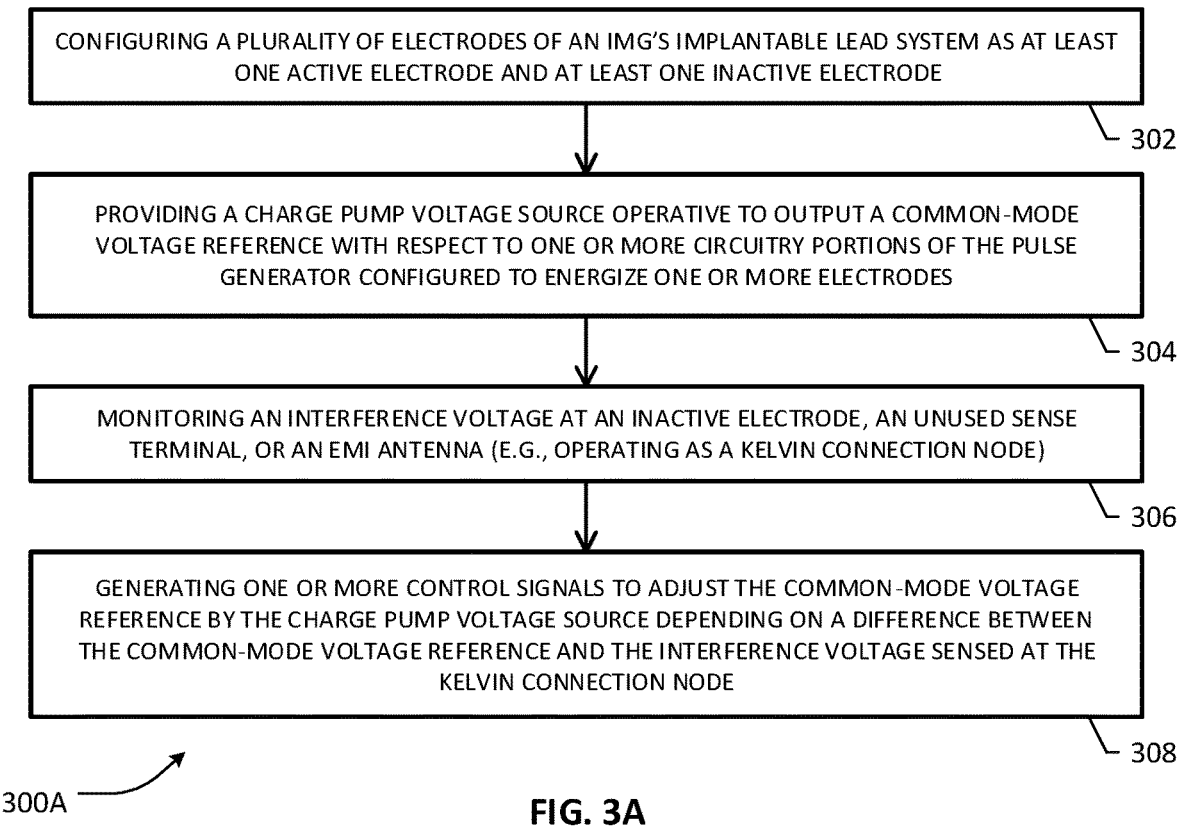
FIG. 3A
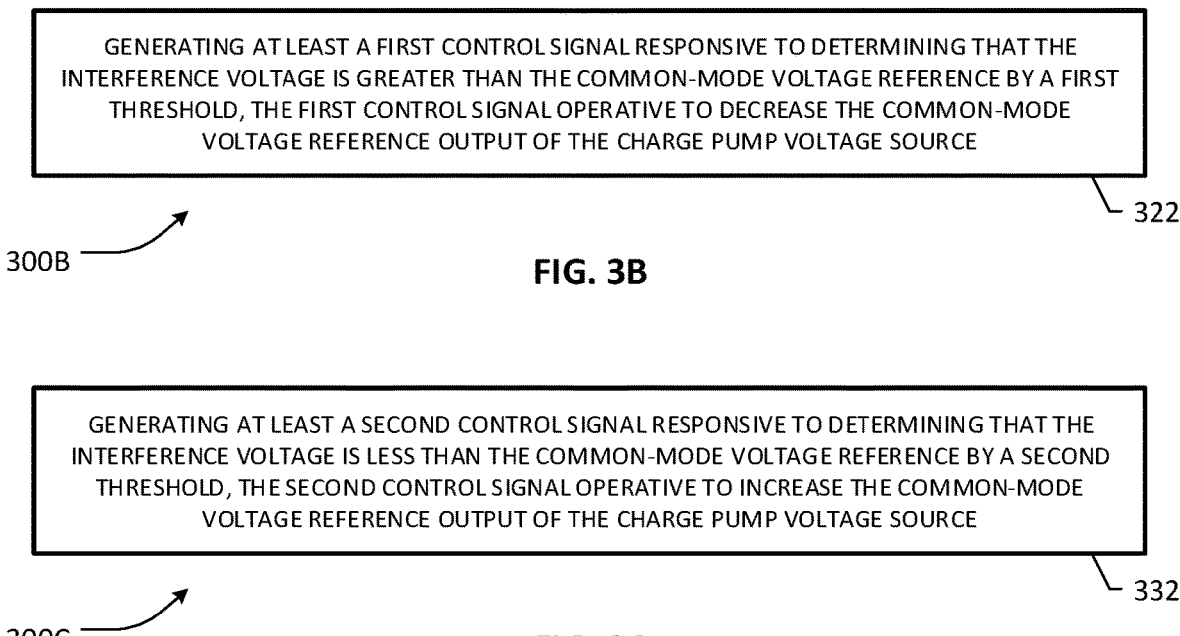
FIG. 3B
FIG. 3C

SETTING A KELVIN CONNECTION SELECTION MODE TO CONFIGURE ONE OR MORE ELECTRODES AND/OR EMI ANTENNA FOR EFFECTUATING APPROPRIATE CONNECTIONS TO DIAGNOSTIC CIRCUITRY COMPARATORS — 402

CONFIGURING AT LEAST ONE INACTIVE ELECTRODE AS A DEDICATED KELVIN CONNECT ELECTRODE OF THE IMPLANTABLE LEAD SYSTEM FOR FACILITATING AT LEAST ONE KELVIN CONNECTION PATH FOR MEASURING/ MONITORING INDUCED VOLTAGE/INTERFERENCE — 412

CONFIGURING AT LEAST ONE ACTIVE ELECTRODE AS ONE OF A CATHODE TO PROVIDE CATHODIC STIMULATION TO THE BIOLOGICAL TISSUE AND AN ANODE TO PROVIDE ANODIC STIMULATION TO THE BIOLOGICAL TISSUE — 422

DIAGNOSTIC CIRCUITRY FOR MONITORING AND MITIGATING ELECTROMAGNETIC INTERFERENCE (EMI) IN AN IMPLANTABLE PULSE GENERATOR

PRIORITY AND CROSS-REFERENCE TO RELATED APPLICATION(S)

This nonprovisional application claims priority based upon the following prior United States provisional patent application(s): (i) "DIAGNOSTIC CIRCUITRY FOR MONITORING AND MITIGATING ELECTROMAGNETIC INTERFERENCE (EMI) IN AN IMPLANTABLE PULSE GENERATOR", Application No. 62/984,607, filed Mar. 3, 2020, in the name(s) of Steven Boor and Daran DeShazo; each of which is hereby incorporated by reference in its entirety.

TECHNICAL FIELD

The present disclosure generally relates to implantable pulse generators and circuitry associated therewith. More particularly, and not by way of any limitation, the present disclosure is directed to diagnostic circuitry for monitoring and mitigating electromagnetic interference (EMI) in an implantable pulse generator (IPG) used in stimulation therapy.

BACKGROUND

The use of electronic stimulation systems to control pain or other indications, or to otherwise provide therapy, by nerve or muscle stimulation has been in use for a number of years. For example, spinal cord stimulation (SCS) is a technique that has been used for pain management since the 1960s. Stimulation systems may also be used in stimulating areas other than the spinal cord, such as for deep brain stimulation, muscle stimulation, etc.

Stimulation systems often comprise a pulse generator coupled to one or more implanted therapy delivery leads having a plurality of electrodes disposed in an area in which neurostimulation is desired. Alternatively, stimulation systems may comprise a micro-stimulation system in which a small implantable housing having electrodes thereon includes a pulse generator, wherein the entire micro-stimulation system is disposed in an area in which neurostimulation is desired. Of course, all or a portion of a stimulation system need not be implanted into a body to provide a desired therapy.

A stimulation system pulse generator may be provided in various configurations, such as a totally implanted pulse generator (IPG) or a radio frequency (RF)-based system. A typical IPG configuration comprises a surgically implanted, internally-powered pulse generator and a multi-electrode lead. A typical RF system configuration comprises a surgically implanted passive receiver and leads, and a transmitter which is worn externally. In operation, the transmitter communicates, through an RF signal, to the implanted receiver to provide stimulation energy and control.

In an SCS application, lead electrodes which are used with an example pulse generator, such as any of the foregoing pulse generators, to deliver a particularized electric field via stimulation to a specific region of the spinal cord or surrounding tissue are considered as the "active" electrodes of the IPG for therapy delivery; unused or "inactive" electrodes are the ones not used for stimulation therapy. Applying such an electric field with the active electrodes across one or more nerve bundles and/or nerve roots, if properly directed and produced at the necessary levels, can "mask" certain forms of chronic pain in a phenomenon referred to as "paresthesia". Similarly, applying an electric field across other tissue, such as muscle or brain matter, near which such electrodes are disposed may provide a desired therapy. The focus, characteristics and intensity of the generated electric field are determined by the electrode configuration (the polarity, if any, assumed by each electrode) and the properties of an electric pulse waveform, which may generally include a stimulation frequency, a stimulation pulse width, a stimulation amplitude, discharge method, and phase information, etc. (collectively "stimulation settings" or "stim-sets").

Conventional IPGs experience certain limitations, particularly in the presence of electromagnetic interference (EMI) including, but not limited to interference caused by magnetic resonance imaging (MRI) scanners. For example, when a patient, who has an implanted IPG, undergoes an MRI scan, the EMI from the MRI system may generate unwanted voltage potentials within the IPG and across the electrodes of a stimulation lead. Among other issues, if the IPG continues to attempt to deliver a stimulation therapy while a patient is undergoing an MRI scan, the EM fields from the MRI scanner may induce added voltage potentials across the electrodes, thereby changing the magnitude and nature of the delivered therapy in an unpredictable, undesired and uncontrollable manner.

To avoid an unpredictable, uncontrolled or undesirable electrode current flow before, during or after stimulation delivery of the therapy to patient tissue, many conventional IPG systems have stimulation therapy turned off during an MRI scan. Additionally, or alternatively, the IPG may be programmed to include a separate special therapy that is configured specifically for the purpose of being delivered during the presence of an MRI scan. Adding a stimulation therapy specifically tailored to an MRI scan introduces an undesired cost and additional burden in the programming of the IPG, as well as may require additional memory and/or circuitry to implement the MRI specific therapy.

SUMMARY

Embodiments of the present patent disclosure are broadly directed to implantable pulse generators or other medical devices, biostimulation systems and associated circuitry wherein various types of Kelvin connection schemes may be provided for measuring and monitoring induced interference voltages and for mitigating the effects of such voltages in the IPG circuitry. Diagnostic circuitry operative with a Kelvin connection scheme may be provided for sensing an interference voltage induced at a Kelvin connect electrode of the IPG's lead system, wherein the diagnostic circuitry is configured to generate one or more control signals for adjusting in substantially real time a common-mode voltage reference operating as a biasing voltage to the IPG circuitry.

In one aspect, an implantable medical device (IMD) having advanced/enhanced diagnostic capabilities is disclosed. According to an example embodiment, the IMD comprises, inter alia, a power supply module; a processing unit; a pulse generator; and an implantable lead system including at least one lead having a plurality of electrodes adapted to stimulate a patient's tissue responsive to instructions generated by the processing unit in association with the pulse generator module, the plurality of electrodes including at least one inactive electrode and at least one active electrode. The IMD also includes a charge pump voltage source operative to supply a common-mode voltage reference with respect to one or more circuitry portions of the pulse generator module configured to energize one or more electrodes. The IMD further includes diagnostic circuitry configured to generate one or more control signals for adjusting the common-mode voltage reference provided by the charge pump voltage source depending on a difference between the common-mode voltage reference and an interference voltage sensed at a Kelvin connection node associated with the lead system. In one example embodiment, the diagnostic circuitry comprises a first comparator having a first reference input and a first sense input; and a second comparator having a second reference input and a second sense input, wherein the first and second sense inputs are commonly coupled to the Kelvin connection node of the implantable lead system and the first and second reference inputs are coupled to respective threshold voltage references. In one example embodiment, the first comparator of the diagnostic circuitry is configured to generate at least a first control signal responsive to determining that the interference voltage is greater than the common-mode voltage reference by a first threshold, wherein the first control signal comprises a 1-bit digital control signal operative to decrease the common-mode voltage reference output of the charge pump voltage source by a predetermined voltage step. In one example embodiment, the second comparator of the diagnostic circuitry is configured to generate at least a second control signal responsive to determining that the interference voltage is less than the common-mode voltage reference by a second threshold, wherein the second control signal comprises a 1-bit digital control signal operative to increase the common-mode voltage reference output of the charge pump voltage source by a predetermined voltage step. In one variation, the IMD may also comprise a mode selector operative to configure different combinations of Kelvin connection nodes, e.g., comprising either direct current (DC) blocking stimulation capacitor ($C_{DC}$) terminals or alternating current (AC) coupling sense capacitor ($C_{SENSE}$) terminals of unused/inactive electrodes, unused $C_{SENSE}$ terminals of active electrodes, or a separate EMI antenna, for measuring/sensing induced interference voltages according to the teachings herein.

In another aspect, diagnostic circuitry and associated method is disclosed for monitoring and mitigating EMI in an IMD's implantable lead system. In one embodiment, the diagnostic circuitry may be configured to perform a method comprising, inter alia, monitoring an interference voltage sensed at a Kelvin connection node associated with the lead system, and generating one or more control signals to adjust a common-mode voltage reference provided by a charge pump voltage source depending on a difference between the common-mode voltage reference and the interference voltage sensed at the Kelvin connection electrode, wherein the common-mode voltage reference is operative as a biasing voltage for current regulator circuitry of the IMD. In one example embodiment, the one or more control signals may comprise at least a first control signal generated by a first comparator responsive to determining that the interference voltage is greater than the common-mode voltage reference by a first threshold, wherein the first control signal comprises a 1-bit digital control signal operative to decrease the common-mode voltage reference output of the charge pump voltage source by a predetermined voltage step. In one example embodiment, the one or more control signals may comprise at least a second control signal generated by a second comparator responsive to determining that the interference voltage is less than the common-mode voltage reference by a second threshold, wherein the second control signal comprises a 1-bit digital control signal operative to increase the common-mode voltage reference output of the charge pump voltage source by a predetermined voltage step.

Additional/alternative embodiments, features, aspects, variations, utilities and advantages of the present disclosure will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

FIGS. 3A-3C depict flowcharts illustrative of blocks, steps and/or acts that may be (re)combined in one or more arrangements with or without other flowcharts for monitoring and mitigating induced interference voltages according to some embodiments of the present disclosure;

FIGS. 4A-4C depict additional blocks, steps and/or acts that may be (re)combined in one or more arrangements with or without other flowcharts of the present disclosure according to some additional embodiments;

DETAILED DESCRIPTION

Figure 1A:
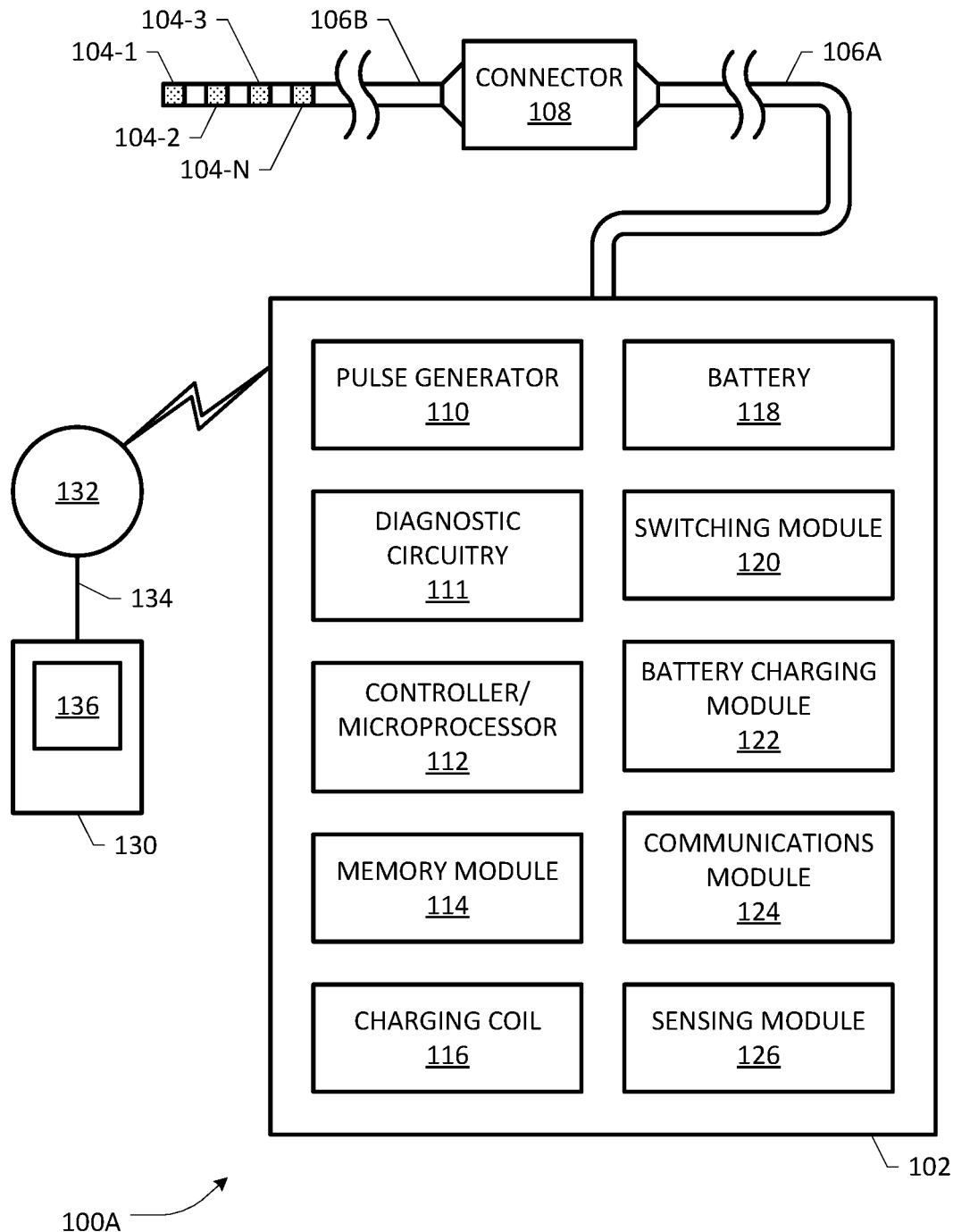
FIG. 1A depicts an example biostimulation system wherein one or more embodiments of a diagnostic circuit of the present disclosure may be practiced in accordance with the teachings herein.

In the description herein for embodiments of the present disclosure, numerous specific details are provided, such as examples of circuits, devices, components and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some embodiments described herein may be particularly set forth in the context of an implantable pulse generator (IPG) for generating electrical stimulation for application to a desired area of a body or tissue based on a suitable stimulation therapy application, such as a spinal cord stimulation (SCS) system. However, it should be understood that example circuitry and methods of operation disclosed herein are not limited thereto, but have broad applicability, including but not limited to different types of implantable devices such as neuromuscular stimulators and sensors, dorsal root ganglion (DRG) stimulators, deep brain stimulators, cochlear stimulators, retinal implanters, muscle stimulators, tissue stimulators, cardiac stimulators, gastric stimulators, and the like, including other bioelectrical sensors and sensing systems, which may be broadly referred to as "biostimulation" applications and/or implantable medical devices (IMDs) for purposes of the present disclosure. Moreover, example circuitry and methods of operation disclosed herein are not limited to use with respect to an IPG or any particular form of IPG. For example, some embodiments may be implemented with respect to a fully implantable pulse generator, a radio frequency (RF) pulse generator, an external pulse generator, a micro-implantable pulse generator, inter alia.

Referring to FIG. 1A in particular, depicted therein is a biostimulation system or IMD system 100A wherein one or more embodiments of a diagnostic scheme or circuit of the present patent disclosure may be practiced for monitoring and mitigating interference voltages induced on one or more implanted lead electrodes associated with a pulse generator in accordance with the teachings herein. By way of illustration, system 100A may be adapted to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, as noted above. System 100A includes an implantable pulse generator (IPG) or IMD 102 that comprises a diagnostic circuit module 111 adapted to effectuate Kelvin connections with one or more electrodes of an implantable lead system and/or an EMI antenna for facilitating measurement of interference voltages (e.g., induced by an external event such as an MRI scan or other EMI event) sensed at or on the electrodes/leads as will be set forth in additional detail further below. In one example embodiment, IPG 102 may be implemented as having a metallic housing or can that encloses a controller/processing block or module 112, pulse generating circuitry 110, a charging coil 116, a battery or power supply 118, a far-field and/or near field communication block or module 124, battery charging circuitry 122, switching circuitry 120, sensing circuitry 126, a memory module 114, and the like. Controller/processor module 112 typically includes a microcontroller or other suitable processor for controlling the various other components of IPG/IMD 102. Software/firmware code may be stored in memory 114 of IPG 102, which may be integrated with the controller/processor module 112, and/or other suitable application-specific storage components (not particularly shown in this FIG.) for execution by the microcontroller or processor 112 and/or other programmable logic blocks to control the various components of the device for purposes of an embodiment of the present patent disclosure.

In one arrangement, IPG 102 may be coupled to a separate or an attached extension component 106A for providing electrical and physical connectivity to an implantable lead system 106B via a lead connector 108, wherein a distal end of the lead 106B includes a plurality of electrodes 104-1 to 104-N. Where the extension component 106A is provided as a separate component, the extension component 106A may connect with a "header" portion of IPG 102 as is known in the art. If the extension component 106A is integrated with IPG 102, internal electrical connections may be made through respective conductive components. In general, electrical pulses are generated by the pulse generating circuitry 110 under the control of processing block 112, and are provided to the switching circuitry 120 that is operative to selectively connect to electrical outputs of the IPG device, which are ultimately coupled to the electrodes 104-1 to 104-N at a distal end of the lead system 106B via respective electrical conductive traces.

In one arrangement, lead electrodes 104-1 to 104-N may be positioned along an axis of the lead 106B, with an angular offset such that the lead electrodes 104-1 to 104-N do not overlap. The lead electrodes 104-1 to 104-N may be in the shape of a ring such that each lead electrode continuously covers the circumference of the exterior surface of the lead 106B. Typically, the lead electrodes 104-1 to 104-N are separated from each other by non-conducting portions of the lead 106B, which electrically isolate each lead electrode 104-1 to 104-N from an adjacent lead electrode 104-1 to 104-N. The non-conducting portions of the lead 106B may include one or more insulative materials and/or biocompatible materials to allow the lead 106B to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane, or the like compositions.

Additionally or alternatively, electrodes 104-1 to 104-N may be in the shape of a split or non-continuous ring such that the stimulation pulse(s) may be emitted in a manner so as to create an electric field emanating in an outward radial direction adjacent to the lead electrodes 104-1 to 104-N. Examples of lead electrodes 104-1 to 104-N and associated fabrication processes are disclosed in one or more of the following: (i) U.S. Patent Application Publication No. 2011/0072657, entitled, "METHOD OF FABRICATING STIMULATION LEAD FOR APPLYING ELECTRICAL STIMULATION TO TISSUE OF A PATIENT"; and (ii) U.S. Patent Application Publication No. 2018/0008821, entitled, "IMPLANTABLE THIN FILM DEVICES", each of which is incorporated herein by reference.

It should be noted the lead electrodes 104-1 to 104-N may be in various other formations, for example, in a planar formation, in an array or grid, etc. on a paddle structure as disclosed in U.S. Patent Application Publication No. 2014/0343564, entitled, "PADDLE LEADS FOR NEUROSTIMULATION AND METHOD OF DELIVERING THE SAME", which is incorporated herein by reference.

In one arrangement, the lead system 106B (as well as extension 106A where provided) may comprise a lead body of insulative material encapsulating a plurality of conductors within the material that extend from a proximal end (that is proximate to IPG 102) to the distal end of the lead body containing the lead electrodes 104-1 to 104-N. The conductors or conductive traces are operative to electrically couple the lead electrodes 104-1 to 104-N to a corresponding plurality of terminals (not shown) of the lead system 106A/B. In a further arrangement, an EMI antenna may be provided (not shown) that may comprise a non-electrode wire or trace conductor within the lead body or routed with insulation substantially alongside external to the lead body. In general, the terminals are adapted to receive electrical pulses from the pulse generation and switching circuitry of IPG 102, which are propagated via the corresponding conductive traces to at least a portion of the lead electrodes 104-1 to 104-N that are adapted to apply the pulses to a desired stimulation target of the patient depending on the particular stimulation therapy application. Also, sensing of physiological or bioelectrical signals may occur through a select number of lead electrodes 104-1 to 104-N, corresponding conductors, and associated terminals. By way of illustration, an example embodiment of the stimulation system 100A may be provided with a plurality of lead electrodes 104-1 to 104-N comprising four electrodes, eight electrodes, etc., although any suitable number of electrodes (as well as corresponding conductive traces and terminals) may be provided in a lead system. Additionally or alternatively, various sensors (e.g., a position detector, temperature sensor, one or more electrochemical sensors, a radiopaque fiducial, etc.) may be located near the distal end of the lead 106B and electrically coupled to terminals through associated conductors within the lead body.

Although not required for all embodiments, the lead body of the implantable lead system 106A/106B may be fabricated to flex and elongate upon implantation or advancing within or relative to the tissue (e.g., nervous tissue) of the patient towards the stimulation target to account for movement of the patient during or after implantation. Fabrication techniques and material characteristics for "body compliant" leads are disclosed in greater detail in U.S. Pat. No. 9,844,661, entitled "COMPLIANT ELECTRICAL STIMULATION LEADS AND METHODS OF FABRICATION", which is incorporated herein by reference.

An example implementation of the components within IPG 102, such as, e.g., processor and associated charge control circuitry for an IPG, is described in U.S. Pat. No. 7,571,007, entitled "SYSTEMS AND METHODS FOR USE IN PULSE GENERATION", which is incorporated herein by reference. An example implementation of circuitry for recharging a rechargeable battery (e.g., battery charging circuitry 122) of an IPG using inductive coupling and external charging circuits is described in U.S. Pat. No. 7,212,110, entitled "IMPLANTABLE DEVICE AND SYSTEM FOR WIRELESS COMMUNICATION", which is incorporated herein by reference. Still further, an example implementation of "constant current" pulse generating circuitry (e.g., at least a portion of pulse generating circuitry 110) is provided in U.S. Patent Application Publication No. 2006/0170486 entitled "PULSE GENERATOR HAVING AN EFFICIENT FRACTIONAL VOLTAGE CONVERTER AND METHOD OF USE", which is incorporated herein by reference. One or multiple sets of such circuitry may be provided within IPG 102 operating in association with a current control module for providing stimulation across a select number of electrodes. Different stimulation pulses on different lead electrodes selected from electrodes 104-1 to 104-N may be generated using consecutively generated pulses according to a "multi-stimset program" as is known in the art. Complex pulse parameters may be employed such as those described in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated herein by reference. Alternatively, multiple sets of such stimulation circuitry may be employed to provide high frequency pulse patterns (e.g., tonic stimulation waveform, burst stimulation waveform, and the like) that include generated and delivered stimulation therapy through one or more leads 104-1 to 104-N as is also known in the art. Various sets of parameters may define the pulse characteristics and pulse timing for the pulses applied to the various lead electrodes as is known in the art. Although constant current pulse generating circuitry is contemplated for some embodiments, any other suitable type of pulse generating circuitry may be employed such as constant voltage pulse generating circuitry.

In an example implementation of IPG 102, sensing circuitry 126 may be provided, preferably adapted to measure a suitable electric parameter or transduced characteristic (e.g., voltage, current, capacitance, etc.) over a configurable time associated with the stimulation target or tissue through at least one of the electrodes proximate to the stimulation target, e.g., electrodes configured to operate as biosensing inputs, wherein such "sensing" electrodes may be coupled to the sensing circuitry 126 via suitable alternating current (AC)-coupling capacitors. In an example embodiment, the sensing circuitry 126 may measure an evoked compound activation potential (ECAP) waveform from an Aβ sensory fiber or spinal cord. Optionally, the sensing circuitry 126 may store the measured/sensed electric data in memory 114. Furthermore, the diagnostic circuitry 111 may be configured to interoperate with the sensing circuitry 126 and pulse generation and switching functionalities of the IPG device 102 for monitoring interference voltages and generating appropriate control signals for purposes of mitigating the effects thereof in the implanted lead system, as will be set forth further below in additional detail.

An external device 130 may be implemented to charge/recharge the battery 118 of IPG 102 (although a separate recharging device could alternatively be employed), to access memory 114, and/or to program or reprogram IPG 102 with respect to the stimulation set parameters including pulsing specifications, ramping sequences, etc., while implanted within the patient. In alternative embodiments, however, separate programmer devices may be employed for charging and/or programming the IPG 102 device and/or any programmable components thereof. An example embodiment of the external device 130 may be a processor-based system that possesses wireline and/or wireless communication capabilities, e.g., a tablet, smartphone, laptop computer, handheld computer, a personal digital assistant (PDA), or any smart wearable device and smart digital assistant device, etc. Software may be stored within a non-transitory memory of the external device 130, which may be executed by the processor to control the various operations of the external device 130. A connector or "wand" 134 may be electrically coupled to the external device 130 through suitable electrical connectors (not specifically shown), which may be electrically connected to a telemetry component 132 (e.g., inductor coil, RF transceiver, etc.) at the distal end of wand 134 through respective communication links that allow bi-directional communication with IPG 102. Optionally, in some embodiments, the wand 134 may comprise one or more temperature sensors for use during charging operations.

In one general scenario, a user (e.g., a doctor, a medical technician, or the patient) may initiate communication with IPG 102 by placing the wand 134 proximate to the stimulation system 100A. Preferably, the placement of the wand 134 allows the telemetry system to be aligned with the far-field and/or near field communication circuitry 124 of IPG 102. The external device 130 preferably provides one or more user interfaces 136 (e.g., touch screen, keyboard, mouse, buttons, scroll wheels or rollers, or the like), allowing the user to operate IPG 102. The external device 130 may be controlled by the user through the user interface 136, allowing the user to interact with IPG 102, including, e.g., dynamically configuring one or more electrodes and/or non-electrode conductive traces (i.e., EMI antenna) for effectuating different Kelvin connection schemes, providing programmatic control for facilitating induced voltage measurements based on applicable equivalent ETI circuit models, etc. as will be set forth further below. Further, the user interface 136 may permit the user to move electrical stimulation along and/or across one or more of the lead(s) 106A using different lead electrode combinations selected from electrodes 104-1 to 104-N, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME", which is incorporated herein by reference. Optionally, the user interface 136 may permit the user to designate which electrodes 104-1 to 104-N are to stimulate (e.g., emit current pulses, in an anode state or in a cathode state), or not selected to stimulate (i.e., remain inactive or floating, i.e., "unused"), with respect to a potential stimulation target, to measure/sense tissue electrical parameters, or the like. As used herein, "stimulation" refers to the application of an electrical signal to a target body tissue, regardless of the effect that signal is intended to produce. Additionally or alternatively, the external device 130 may access or download the electrical measurements from the memory 114 acquired by the sensing circuitry 126 and/or diagnostic circuitry 111.

In some implementations, the external device 130 may permit operation of IPG 102 according to one or more spinal cord stimulation (SCS) programs or therapy applications to treat the patient. Each SCS program may include one or more sets of stimulation parameters of the pulse including pulse amplitude, stimulation level, pulse width, pulse frequency or inter-pulse period, pulse repetition parameter (e.g., number of times for a given pulse to be repeated for respective stimulation sets or stimsets during execution of program), biphasic pulses, monophasic pulses, etc. IPG 102 modifies its internal parameters in response to the control signals from the external device 130 to vary the stimulation characteristics of the stimulation therapy transmitted through the lead system 106A/106B to the tissue of the patient. Example neurostimulation (NS) systems, stimsets, and multi-stimset programs are set forth in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated hereinabove by reference.

It will be appreciated that although example lead system 106A/B shown in FIG. 1A is illustrated with a single implantable lead, the teachings herein are not necessarily limited thereto and an example embodiment of the present invention may involve a lead system comprising two or more implantable leads, which may comprise various types of leads such as paddle leads, percutaneous leads, etc., with each lead having a respective plurality of electrodes, with or without a separate EMI antenna trace, wherein different types of Kelvin connection paths may implemented for measuring induced interference voltages/charge states in accordance with the teachings herein.

It is known that in providing a stimulation signal to a target body tissue, an accumulation of continuous or net charge at the electrode/tissue interface may occur, resulting in a residual voltage, which may not only dynamically affect the electrical characteristics of stimulation pulses being applied but also contribute to deterioration of lead electrode integrity. To maintain charge balance, accordingly, some arrangements of IPG 102 may include output coupling capacitors between the output circuits of the pulse generation/switching circuitry and the electrodes to block errant continuous direct current (DC) for the electrical signals being applied to the tissue. In such arrangements, charge built up on the electrodes during stimulation may be offset by use of such output coupling capacitors (DC blocking stimulation capacitors), and may be discharged when delivery of a portion of the electrical signal is completed, e.g., typically after delivery of an individual pulse in a stimulation signal. A "discharge phase" may be observed for a period, for example, after a monophasic stimulation phase. In one arrangement, the stimulation phase and the discharge phase taken together may be considered a charge-balanced pulse in a signal comprising a plurality of such pulses. Even in such arrangements, however, there may be a gradual buildup of residual voltage across the DC blocking stimulation capacitors over time, depending on the frequency and type of pulsing schemes and associated stimsets used, in addition to the charge/voltage buildup at the ETI of an implantable lead system.

Figure 1B:
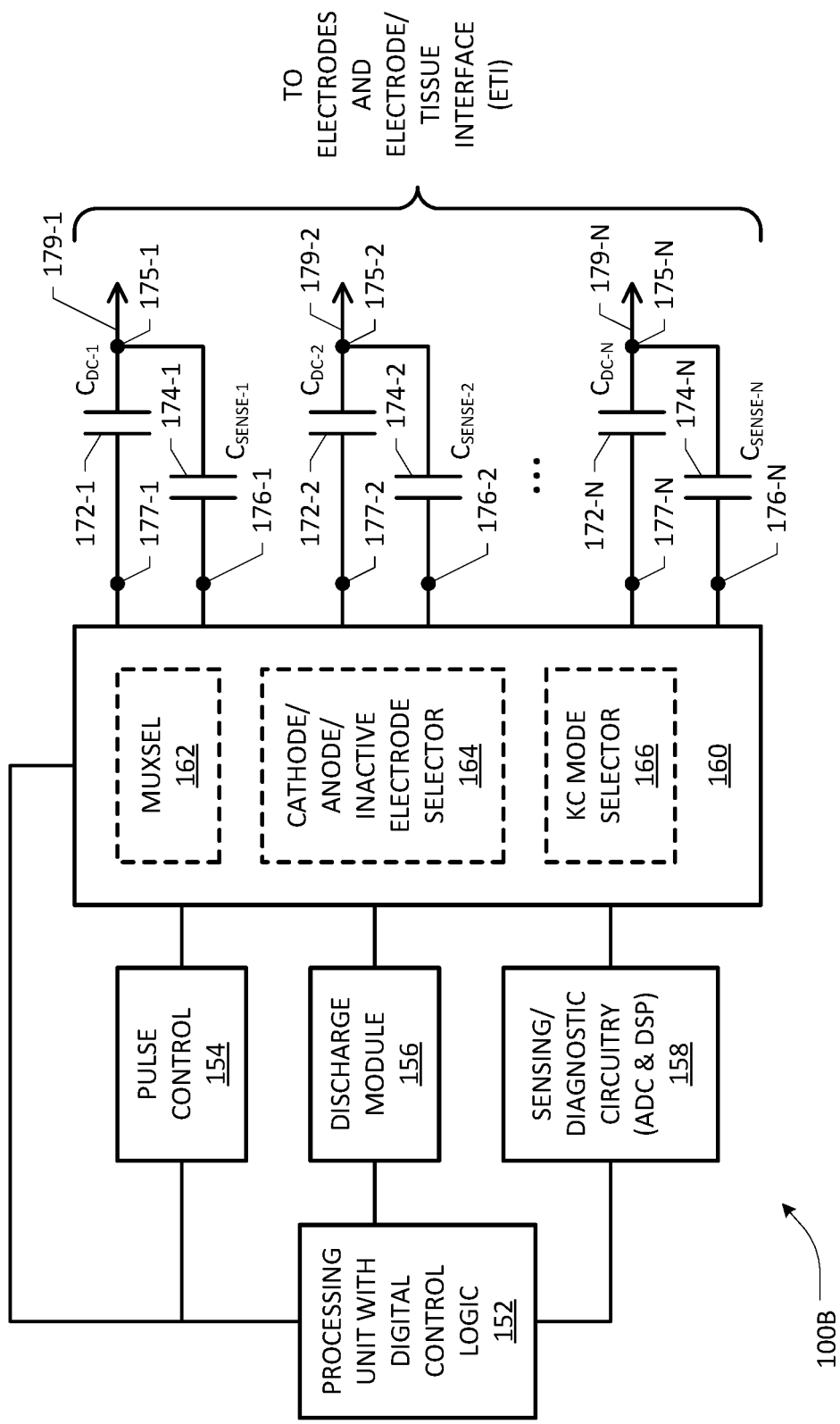
FIG. 1B depicts a pulse generator portion having diagnostic circuitry and associated lead electrode capacitor arrangement for purposes of an embodiment of the present disclosure.

Turning to FIG. 1B, depicted therein is a pulse generator portion 100B having diagnostic circuitry and associated lead electrode capacitor arrangement for purposes of an embodiment of the present disclosure. One skilled in the art will recognize upon reference hereto that various functionalities and structural components associated with example blocks shown as part of the pulse generator portion 100B may be distributed, integrated and/or otherwise (re)arranged among one or more blocks, subsystems and/or modules described hereinabove with respect to FIG. 1A. Consistent with the description set forth previously, a processing unit 152 having or associated with suitable digital control logic is operatively coupled to pulse control module 154, discharge module 156 and sensing/diagnostic circuitry 158 for facilitating various functionalities including but not limited to effectuating induced interference voltage measurements and comparisons, active discharge cycling, electrode selection and configuration for establishing Kelvin connections, etc., as well as generating appropriate control signals for adjusting a common-mode voltage reference used for suitably biasing floating power supplies used in current regulator circuitry (not specifically shown in this FIG.), preferably under appropriate programmatic control. An input/output (I/O) interface block 160 is operatively coupled to a plurality of lead connectors 179-1 to 179-N comprising a lead system interfaced with respective electrodes and associated ETI that may be represented as circuitry based on known or heretofore unknown charge-transfer mechanisms or models (not shown in this FIG.). Each lead connector 179-1 to 179-N may be provided with a DC blocking stimulation capacitor ($C_{DC}$) for facilitating direct current flow blocking functionality with respect to the corresponding electrode that may be configured to operate as a stimulation node. In some embodiments, an AC-coupling sense capacitor ($C_{SENSE}$) may be optionally provided for facilitating AC-coupling functionality with respect to an electrode that may be configured to operate as a stimulation node or a sensing node. By way of illustration, DC blocking stimulation capacitor $C_{DC-1}$ 172-1 and sense capacitor $C_{SENSE-1}$ 174-1 are coupled to lead connector 179-1 such that two interface terminals 177-1 and 176-1 are effectuated with respect to the lead circuitry of the interface block 160. Sense capacitor $C_{SENSE-1}$ 174-1 is configured with $C_{DC-1}$ 172-1 such that an intermediate tap or node 175-1 is effectuated on the lead connector 179-1. Likewise, remaining lead connectors 179-N may be provided with respective $C_{SENSE-N}$ capacitors 174-N configured with corresponding $C_{DC-N}$ capacitors 172-N to facilitate two interface terminals or nodes 177-N and 176-N for each corresponding lead electrode connector. As will be seen below, such an arrangement can facilitate a Kelvin connection terminal via either of the $C_{DC}$ or $C_{SENSE}$ terminals of an unused electrode or an unused $C_{SENSE}$ terminal of an active electrode for facilitating an induced voltage measurement loop in some embodiments. Although the illustrated embodiment of FIG. 1B exemplifies an arrangement where each lead connector is provided with a corresponding sense capacitor, it should be appreciated that other arrangements may be realized within the scope of the present patent disclosure where not all lead connectors are coupled to and/or provided with respective sense capacitors.

Interface block 160 may include appropriate multiplexing and selection circuitry 162, anode/cathode/inactive electrode selection circuitry 164 and Kelvin connection (KC) mode selection circuitry 166 for effectuating various types of Kelvin connection schemes for measurement purposes while different electrodes of a lead system may be selectively configured for stimulation (e.g., anodic or cathodic stimulation), sensing, or designating unused/inactive states, etc., with appropriate electrical connections being made within an IPG device accordingly relative to the various components therein, under suitable programmatic control as needed. Example diagnostic circuitry 158 may comprise suitable analog-to-digital converter (ADC) circuitry and/or voltage comparator circuitry operative with suitable threshold references with respect to comparing induced voltages within certain guard bands. As such, voltage comparator circuitry can be external and/or internal, on-board or off-board, and/or may be coupled to other measurement devices.

Figure 1C:
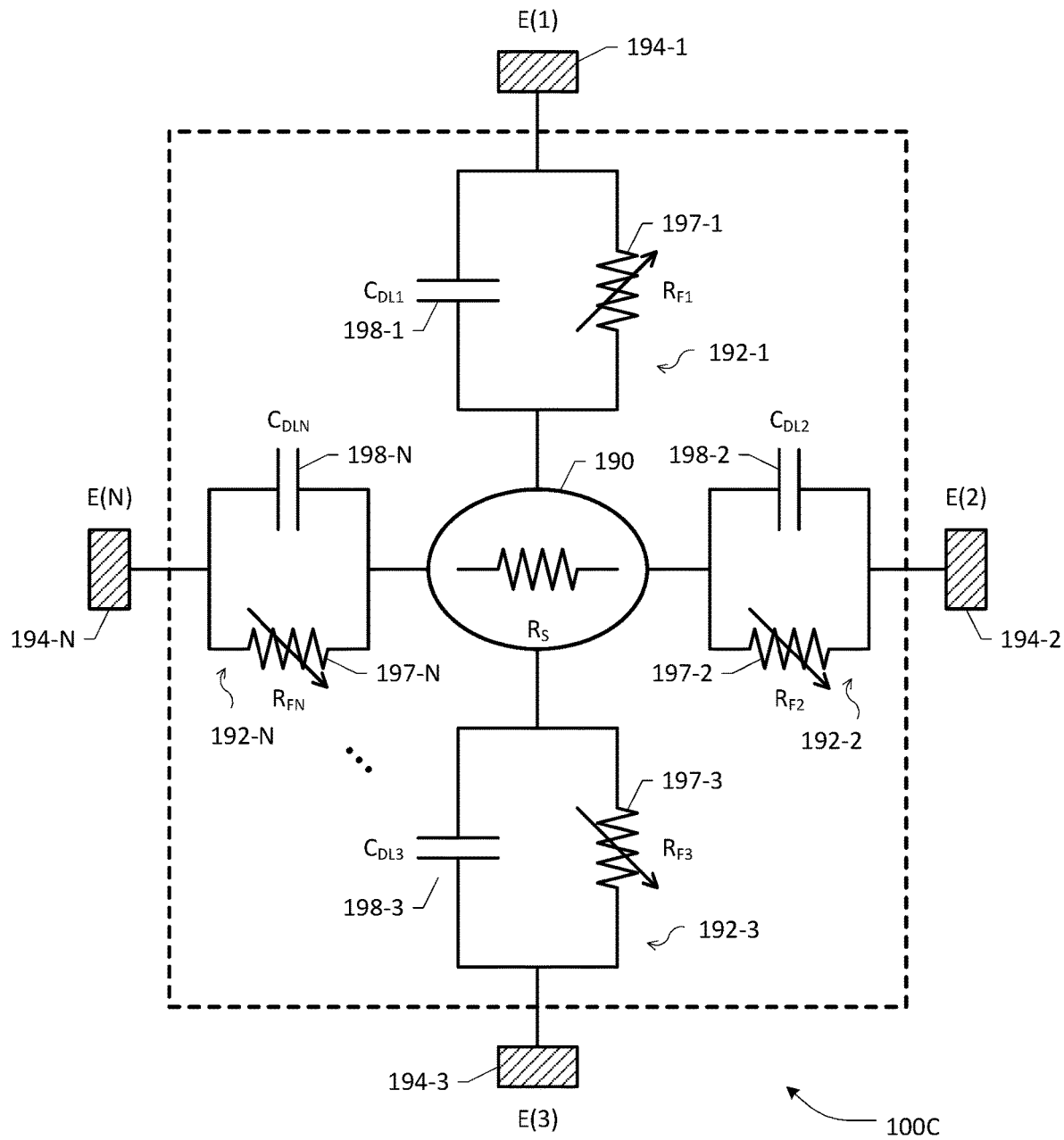
FIG. 1C depicts a generalized electrode/tissue interface (ETI) equivalent circuit arrangement for an IMD's lead electrode system wherein a Kelvin connection scheme may be implemented in conjunction with suitable diagnostic circuitry for monitoring and mitigating induced interference voltages according to an embodiment of the present disclosure.

When an electrode is placed near tissue, current flow is determined by the flow of electrons in the electrode and flow of ions in the tissue. The electrode/electrolyte (i.e., tissue) interface (EEI or ETI; also sometimes referred to as electrode/patient interface or EPI) is typically modeled in accordance with a linear lumped element charge transfer model (e.g., Randles equivalent circuit of the electrode-electrolyte interface), involving a series of lumped resistor elements coupled with a shunt capacitance that models the double layer of charge at the interface. FIG. 1C depicts a generalized ETI equivalent circuit arrangement 100C for an IMD's lead electrode system for purposes of an embodiment of the present disclosure. In the illustrated arrangement 100C, the solution resistance, $R_S$, is representative of the bulk electrolyte, which models the tissue or patient resistance, $R_{PATIENT}$, as a pure resistive component 190 disposed across electrodes E(1) 194-1 to E(N) 194-N. With respect to each electrode, a double-layer capacitance or $C_{DL}$ models the double layer of charge at the interface, which is coupled in parallel to a charge transfer resistance $R_{CT}$, also referred to as Faradaic resistance ($R_F$), across the interface. Faradaic resistance, $R_F$, in parallel with the capacitance, $C_{DL}$, accounts for the conduction of charge through the interface, which can occur through various mechanisms, e.g., typically through oxidation-reduction reactions at the electrode for efficient operation of stimulation electrodes. Reference numerals 192-1 to 192-N shown in FIG. 1C accordingly refer to equivalent circuit representations of ETIs associated with corresponding electrodes 194-1 to 194-N, respectively, wherein $C_{DL1}$ 198-1 to $C_{DLN}$ 198-N and $R_{F1}$ 197-1 to $R_{FN}$ 197-N are illustrative of the respective lumped capacitive and resistive components thereof. Whereas more complex models of the electrode/tissue interface may be used, the foregoing charge transfer model is illustrated herein without necessarily being limited thereto for purposes of exemplifying how a Kelvin connection path may be advantageously effectuated in an implanted lead system for monitoring an induced interference voltage due to an EMI event. A "Kelvin connection" for purposes of the present patent disclosure is a circuit arrangement that allows avoiding voltage drops (thereby current flows) in circuit segments in a measurement or instrumentation circuit path that may interfere with or confound measurement variables. Some example embodiments disclosed herein utilize such connection arrangements by employing either unused DC blocking stimulation capacitor paths and/or unused AC-coupling sense capacitor paths associated with respective electrodes (shown in FIG. 1B) as a Kelvin connection path or node in a voltage comparison circuit measurement path for monitoring induced interference voltages. In still further example embodiments, a separate MRI antenna may be utilized as a Kelvin connection node for monitoring interference voltages as set forth in U.S. patent application Ser. No. 16/401,943, filed May 2, 2019, entitled, "NEUROSTIMULATION METHOD AND SYSTEM FOR ACTIVE EMULATION OF PASSIVE DISCHARGE IN PRESENCE OF MRI/EMI INTERFERENCE", which is incorporated by reference herein.

Figure 2A:
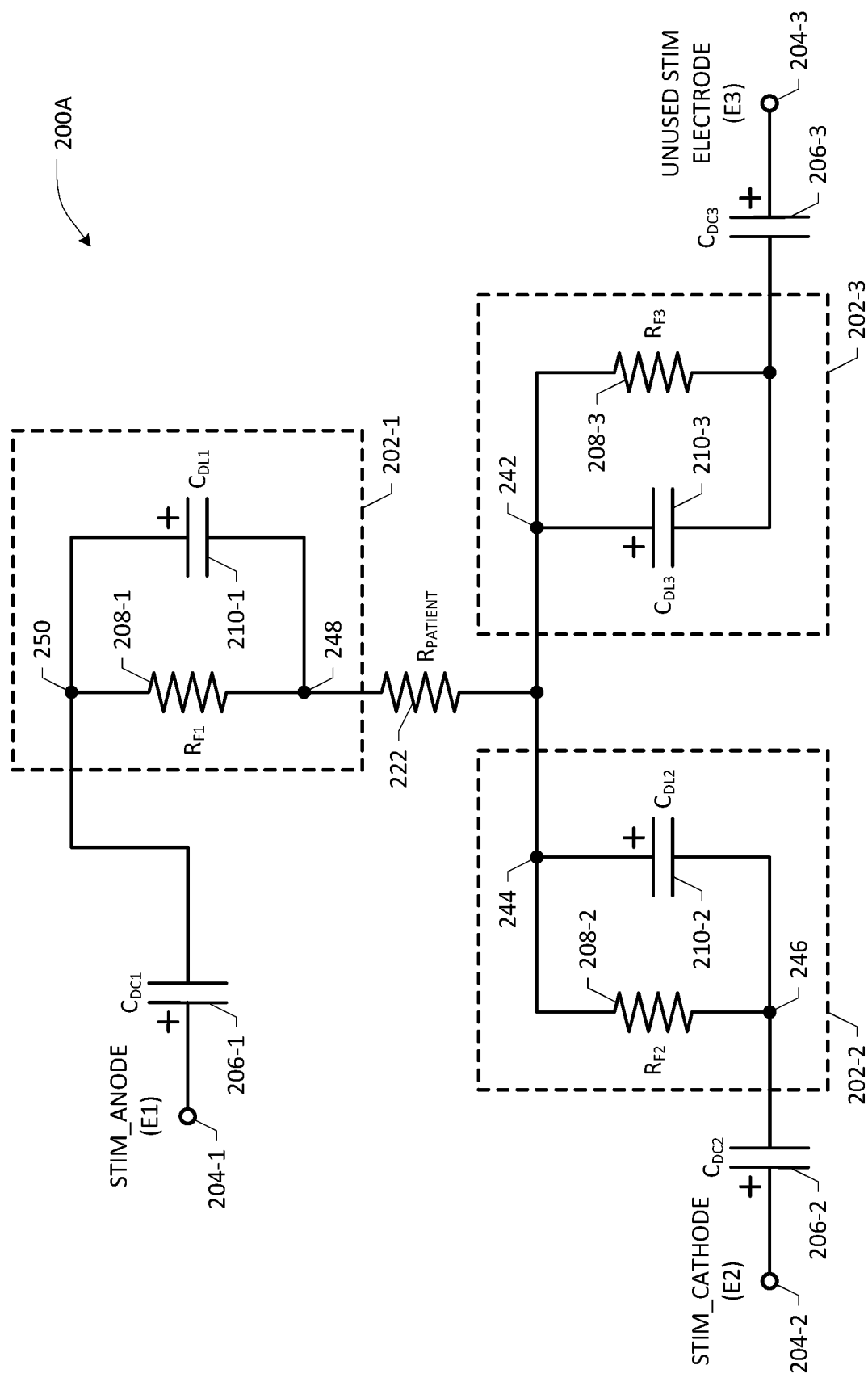
FIG. 2A depicts an example equivalent ETI circuit diagram associated with a sample electrode system using one type of Kelvin connection path for purposes of an embodiment of the present disclosure.

FIG. 2A depicts an example equivalent ETI circuit diagram 200A associated with a sample electrode system using one type of Kelvin connection path for purposes of an embodiment of the present disclosure. Three electrodes (E1, E2 and E3) and respective tissue interfaces 202-1 to 202-3 are shown by way of example. Illustratively, electrodes E1 and E2 are configured as stimulation anode and cathode, respectively, with electrode E3 being left unused or inactive. Each electrode is provided with a respective DC blocking stimulation capacitor $C_{DC}$, which facilitates a terminal or node with respect to an IPG interface block coupled to suitable diagnostic/sense circuitry as described previously. Further, each ETI 202-1 to 202-3 is exemplified by a corresponding $C_{DL}$ 210-1 to 210-3 coupled in parallel to respective charge transfer resistance $R_F$ 208-1 to 208-3 that is in series connection with the bulk patient resistance $R_{PATIENT}$ 222. Because E3 is configured as an unused electrode for stimulation, its DC blocking stimulation capacitor $C_{DC3}$ 206-3 is kept in a discharged state, which allows the associated terminal 204-3 to be used in a Kelvin connection path with respect to a measurement circuit loop. As will be seen below, such a measurement circuit loop may involve voltage comparator circuitry configured to monitor EMI-induced voltages in an IPG and generate appropriate control signals for effectuating EMI mitigation.

In some arrangements, lead electrodes may be provided with respective AC-coupling sense capacitors also, as noted above with respect to FIG. 1B. Because an inactive electrode may also be provided with an AC-coupling sense capacitor path (which is a likely implementation scenario since it is preferable to manufacture identical electrodes in a lead system that can be selectively and dynamically configured depending on a particular stimulation application and associated stimset variations), an alternative Kelvin connection path may be established at the inactive electrode in addition to the inactive DC blocking stimulation $C_{DC}$ capacitor path thereat in some further embodiments. In an additional/alternative arrangement, one of the electrodes of a lead system or an EMI antenna may be designated or dedicated to operate as a Kelvin connection terminal with respect to a measurement circuit loop. Still further, an unused AC-coupling sense capacitor terminal of an active electrode may also be used as a Kelvin connection terminal, as will be set forth below. One skilled in the art will therefore readily appreciate that a number of Kelvin connection modes may be effectuated in an example IMD/IPG system depending on the various AC-coupling and/or DC blocking stimulation capacitor arrangements provided with respect to the electrodes of a lead system and/or how the different electrodes and corresponding capacitor arrangements are selectively configured. Accordingly, as used herein, the term "Kelvin connect" electrode or "Kelvin connection node" may include any of the foregoing electrical node arrangements disposed in a measurement circuit loop based on a Kelvin connection path.

Figure 2B:
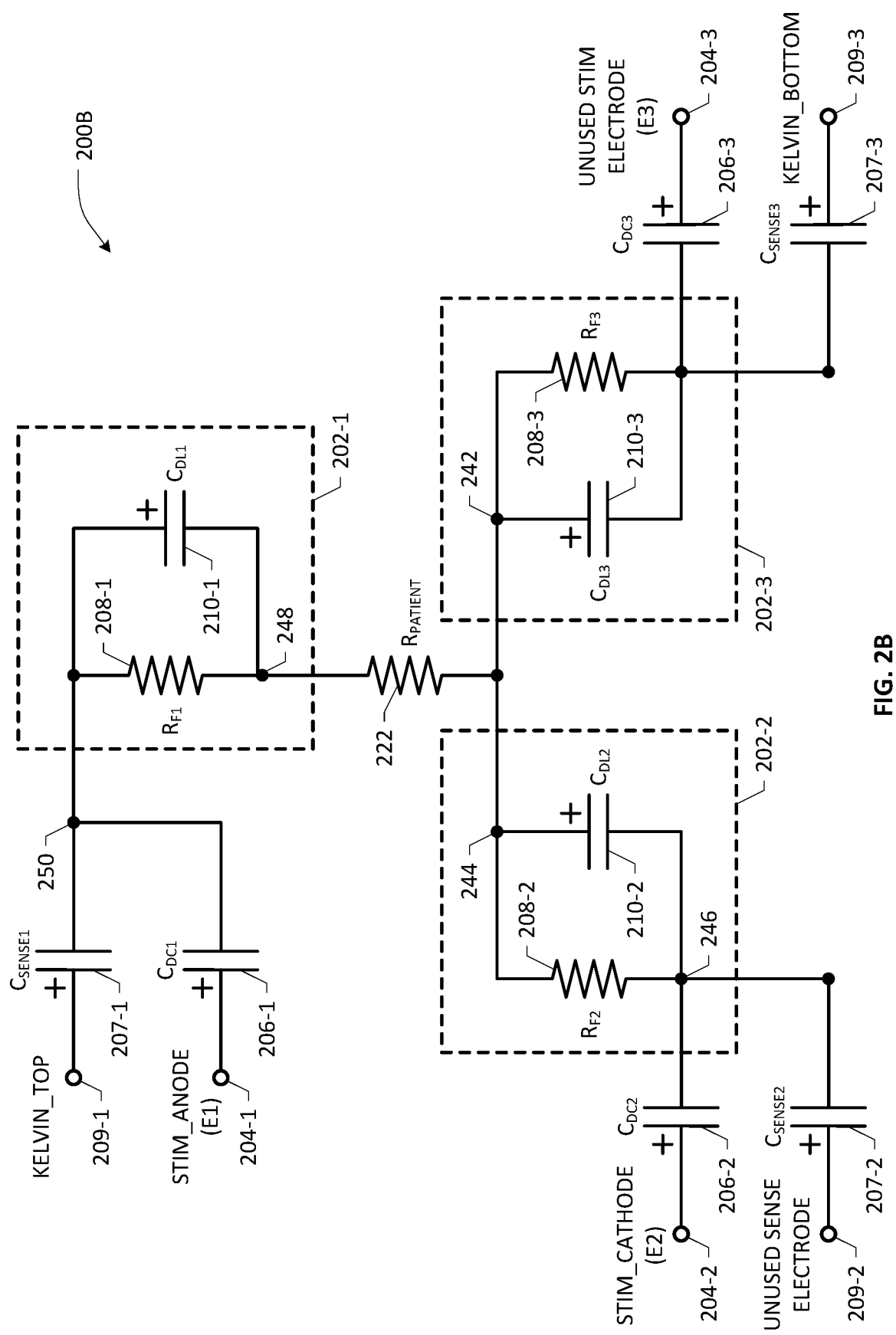
FIG. 2B depicts an example equivalent ETI circuit diagram associated with a sample electrode system using a combination of Kelvin connection paths for purposes of an embodiment of the present disclosure.

Turning to FIG. 2B, depicted therein is an example equivalent ETI circuit diagram 200B associated with a sample electrode system that illustrates different types and/or combinations of Kelvin connection paths for purposes of an embodiment of the present patent disclosure. Similar to the arrangement 200A illustrated in FIG. 2A, circuit arrangement 200B of FIG. 2B exemplifies three electrodes, E1-E3, each shown with corresponding ETI circuit representations 202-1 to 202-3 coupled to bulk patient resistance $R_{PATIENT}$ 222 in a "star" configuration. Further, electrodes E1 and E2 are illustrated as active stimulation nodes while electrode E3 is left as an inactive/unused electrode as before. Each electrode is provided with corresponding biosensing input terminal 209-1 to 209-3, effectuated via respective AC-coupling capacitors $C_{SENSE1}$ 207-1 to $C_{SENSE3}$ 207-3 that are coupled in parallel to the respective DC-blocking capacitors, $C_{DC1}$ 206-1 to $C_{DC3}$ 206-3. In one embodiment, the AC-coupling capacitors $C_{SENSE1}$ 207-1 to $C_{SENSE3}$ 207-3 may be implemented as low capacitance components (e.g., around 0.1 μF), which may be maintained to be readily kept in a discharged state (e.g., because no stimulation current will flow through such capacitors). Accordingly, voltage levels at the AC-coupling capacitors $C_{SENSE1}$ 207-1 to $C_{SENSE3}$ 207-3 of electrodes E1-E3 are near or close to 0 V (or some other reference potential), which can facilitate respective Kelvin connection terminals thereat.

For example, terminal 209-3 associated with $C_{SENSE3}$ 207-3 of the unused electrode E3 (which is at the same potential as internal node 242) may be used as a Kelvin connect electrode with respect to a voltage measurement loop. Likewise, the $C_{DC3}$ terminal 204-3 of the unused electrode E3 may also be used a separate Kelvin connect electrode in a voltage measurement loop in an alternative embodiment, as previously described. Skilled artisans will recognize this alternative Kelvin connection path may be beneficial to use if the biosensing AC-coupling $C_{SENSE3}$ 207-3 terminal 209-3 associated with electrode E3 is already in use for biosensing and it is required that the sensing activity from electrode E3 remain undisturbed. In a further arrangement, the unused $C_{SENSE2}$ capacitor terminal 209-2 of the electrode E2 (which may be configured to be active for providing stimulation) may also be used as yet another Kelvin connect electrode with respect to the sample lead electrode system illustrated in FIG. 2B. Additional details regarding implementing Kelvin electrode connections in an IPG and associated lead systems comprising one or more leads may be found in U.S. patent application Ser. No. 16/195,502, filed Nov. 19, 2018, entitled, "KELVIN CONNECTION SCHEME FOR DIAGNOSTIC CAPABILITY IN A NEUROSTIMULATOR", which is incorporated by reference herein.

According to example embodiments herein, one or more Kelvin connect electrodes of an IPG's lead system can be utilized in conjunction with suitable diagnostic circuitry in a Kelvin connection measurement loop in order to sense and mitigate interference voltages induced by EMI in the IPG system. Further, one or more Kelvin connect electrodes or unused sense capacitor terminals may be used as an EMI antenna in some embodiments as previously noted. Additionally or alternatively, an EMI antenna may be constructed as a "dummy" wire (also referred to as a non-electrode wire) provided within the lead or routed with insulation substantially alongside the outside of the lead and arranged to extend alongside other stimulation wires in the lead as noted elsewhere in the present patent disclosure. The dummy wire may not electrically conduct with human tissue, and thus may not be considered to be an "electrode" in a strict sense. As will be set forth hereinbelow, an example IMD/IPG system may be configured to utilize any of the foregoing arrangements in association with appropriate diagnostic circuitry to facilitate EMI sensing and mitigation.

Among other things, embodiments herein utilize the insight that, during an MRI scan or other type of EMI event (collectively EMI), the interference voltages induced on each electrode and/or associated conductor trace of an IMD/IPG are generally very similar (e.g., nearly identical) and/or exhibit a common-mode characteristic across all electrodes. More specifically, the EMI induces similar voltage variations at each of the electrodes at any given instant in time. Embodiments herein utilize the foregoing concept by designating an inactive or unused electrode, or an unused sense capacitor terminal of an electrode, or an EMI antenna, as a Kelvin connect node to provide a sense signal indicative of an induced interference voltage, which may be processed by a diagnostic circuit to generate appropriate feedback control signals to a common-mode voltage supply operative to provide a baseline voltage reference with respect to a current regulator used in the IPG for providing stimulation currents. Accordingly, such a common-mode voltage supply may be modulated appropriately in the presence of EMI in order that an optimal range of operating voltages (also referred to as "headroom") may be maintained in the IPG circuitry, including any protection circuitry provided therein, thereby alleviating the deleterious effects of voltage excursions caused by any interference during, before or after stimulation therapy.

Broadly, a tandem pair of comparators may be provided as part of a diagnostic circuit according to an example embodiment, wherein the comparators can be configured to generate control signals for monitoring and counteracting the amount of interference voltage from an EMI event being induced upon a Kelvin connect electrode in a stimulation lead. In one arrangement, the comparators may be configured to generate digital control signals comprising an UP control signal and a DOWN control signal, which can be used to increase or decrease the voltage output of a very low power charge pump voltage source operating as a common-mode voltage reference supply whenever the amount of interference on the Kelvin connect electrode is different from the common-mode reference voltage by a predetermined threshold that may be configurable depending on implementation. Accordingly, such a common-mode voltage reference may be generated and modulated to bias the IPG circuitry for providing optimal operating headroom, and to inversely track the induced interference voltages on a stimulation lead within the predetermined threshold guard band (that may be symmetric, e.g., ±1 volt, or otherwise), which is generally adequate for mitigating the deleterious effects of interference from MRI/EMI. Because a common-mode voltage reference may be generated by a charge pump, some embodiments may therefore be configured to provide a common-mode voltage reference in both positive and negative voltage ranges (i.e., create an output below the system ground, typically the negative battery voltage) that allows for peak-to-peak signal swings larger than a typical voltage multiplier output (e.g., 15.0 V) used in extant IPG/IMD implementations, which would otherwise limit the reference voltage swing range such that it can diminish the mitigation effect of the common-mode voltage reference modulation.

Figure 5:
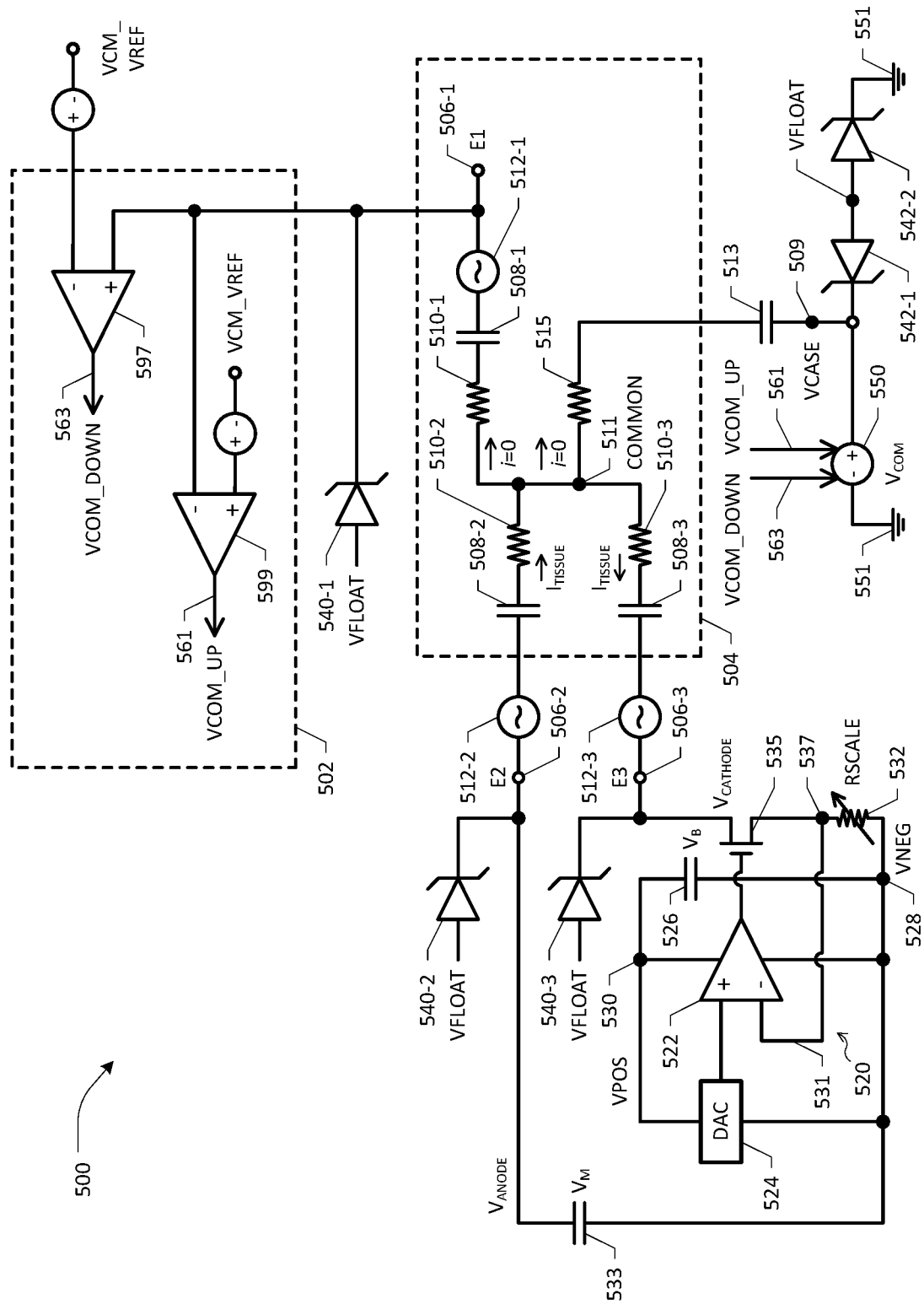
FIG. 5 depicts an example circuit arrangement including a three-electrode lead system represented by a simplified ETI arrangement and associated current regulator circuitry, wherein an embodiment of diagnostic circuitry is provided for monitoring and mitigating interference voltages in an IPG according to an embodiment of the present disclosure.

Attention is directed to FIG. 5, which depicts an example circuit arrangement 500 including a three-electrode lead system represented by an ETI network 504 and associated current regulator circuitry 520, wherein an embodiment of diagnostic circuitry 502 is provided for monitoring interference voltages using a Kelvin connection node according to the teachings herein. One skilled in the art will appreciate that in the example circuit arrangement 500, ETI network 504 is illustrated as a simplified version of the ETI circuit arrangements 200A or 200B shown in FIGS. 2A and 2B, wherein DC blocking $C_{DC}$ capacitors and double-layer $C_{DL}$ capacitors for each electrode E1 506-1 to E3 506-3 are merged into a single capacitor 508-1 to 508-3, respectively. Further, in respect of the Kelvin connection scheme of FIG. 2B, AC-coupling $C_{SENSE}$ capacitors and Faradaic $R_F$ components associated with each electrode are also not shown in this FIG. for sake of simplicity. For purposes of the embodiment of FIG. 5, E1 506-1 is provided as a Kelvin connect electrode (also representative as an EMI antenna), whereas E2 506-2 and E3 506-3 are designated as stimulation electrodes that may be configured to provide appropriate therapy to the patient's tissue.

In general, the circuit arrangement 500 is representative of a IPG stimulation system having a lead system with an array of electrodes (designated, e.g., electrodes E1-E3 and a IPG Case electrode 509 configured to facilitate a common-mode voltage reference path), which may be implanted within a patient and positioned proximate to tissue of interest that is associated with the target region. As a nonlimiting example, the circuit 500 may be configured to deliver a stimulation therapy for use with SCS, DBS, DRG, and the like. For bipolar stimulation, the array of electrodes may includes two or more active electrodes, e.g., E2 506-2 as an anodic electrode for sourcing stimulation current and E3 506-3 as a cathodic electrode for sinking stimulation current, wherein the stimulation therapy is delivered between the active electrodes E2 and E3 via the patient's tissue as represented by the ETI network 504. In the present example, Case electrode 509 is not utilized during bipolar stimulation therapy. Optionally, when monopolar stimulation is delivered, the Case electrode 509 may be utilized as an anode electrode and one or more of the electrodes E1, E2, E3 may be utilized as a cathode electrode. While the examples herein are described in connection with a single electrode E3 as the active cathode electrode and a single electrode E2 as the active anode electrode, it is recognized that in other example embodiments, two or more electrodes may be utilized as anode and/or cathode electrodes that may be commonly or separately energized by appropriate current regulator(s) under suitable program control.

Inactive electrode E1 506-1 is representative of one or more of the inactive electrodes which may be utilized as a Kelvin connect electrode (or EMI antenna) to sense and mitigate interference voltages induced by EMI, as previously noted. In one configuration, the circuit arrangement 500 may be managed by one or more circuitry portions of a IPG pulse generator module, e.g., implemented at least in part by processing unit 152 and pulse control module 154 of FIG. 1B. The circuit arrangement 500 includes a current regulator (CR) circuit 520 that is connected to, and configured to control current flow through, select active electrodes, e.g., E2 and E3, during delivery of the stimulation therapy under direction of suitable control logic, wherein applicable voltage levels for powering the CR circuit may be managed in reference to one or more floating power supplies and one or more floating ground nodes. As illustrated, CR circuit 520 includes an error amplifier 522 that includes power supply terminals that are connected to, and receive power from, a charge pump 526 coupled between a power supply node 530 (also designated as VPOS) and a floating ground node 528 (also designated as VNEG). In one arrangement, the charge pump 526 disposed between the floating ground node 528 and the power supply node 530 may comprise a capacitor or capacitor bank operating under programmatic control that may be selectively charged by a battery of the IPG and is configured to supply a predetermined voltage VB across the power supply terminals of the CR circuit 520. By way of example, the charge pump 526 may emulate the battery voltage in some arrangements. In one arrangement, the charge pump 526 may be intermittently connected to the battery of the IPG during charging operations and disconnected from the battery to allow the charge pump 526 to operate as a floating power supply for the CR circuit 520. In one arrangement, the negative terminals of the charge pump 526 and CR circuit 520 may be commonly connected to the floating ground node 528, thereby enabling the power supply for the CR circuit 520 to move up and down in voltage as desired in accordance with a common-mode reference voltage or voltage reference ($V_{COM}$) supplied by a voltage source 550, without changing a voltage potential across the power supply terminals 530, 528 of the CR circuit 520.

Appropriate switching circuitry with respect to the charge pump 526 and the IPG battery may be provided in one example embodiment to facilitate a floating power supply arrangement for the operation of CR circuit 520. During charging, the negative terminal of the charge pump 526 may be connected to a fixed ground while the charge pump 526 is charged to a desired energy level. Once the charge pump 526 achieves a desired energy charge level, it may be switchably connected to the power supply terminals 530 and 528 of CR circuit 520. Under suitable switch control logic, the charge pump 526 is configured to operate as a floating power supply in that the negative terminal thereof is no longer tied to a fixed ground level. Instead, the floating ground node 528 and associated negative power supply terminal of the charge pump 526 are allowed to float up and down in voltage (relative to a fixed ground). The charge pump 526 thus represents a "floating power supply" as a voltage at the negative terminal of the charge pump 526 (corresponding to the node 528) is permitted to drift, or otherwise fluctuate, upward and downward (relative to a reference ground) and is not tied to a fixed voltage reference (e.g., 0 V). As a further example, when a negative terminal of the battery defines the fixed reference ground, the negative terminal of the charge pump 526 is not directly electrically connected to, and is electrically separate from, the negative terminal of the battery, but instead is allowed to drift upward and downward relative to the reference ground. As will be set forth further below, during an EMI event, the common-mode reference voltage source 550 that provides a baseline average voltage for the floating power supply operating range may be adjusted based on control signals provided by a diagnostic circuit operating in conjunction with the Kelvin connect electrode E1 506-1 for sensing induced voltages so as to maintain a stimulation profile during delivery of the stimulation therapy while in the presence of the EMI event. Additional details regarding a floating power supply system for a CR circuit may be found in U.S. patent application Ser. No. 16/401,971, filed May 2, 2019, entitled, "NEUROSTIMULATION METHOD AND SYSTEM WITH CURRENT REGULATOR BIASED BY A FLOATING POWER SUPPLY", which is incorporated by reference herein.

Continuing to refer to FIG. 5, error amplifier 522 includes first and second input terminals (designated by the positive and negative signs corresponding to non-inverting and inverting inputs, respectively), wherein the first terminal is connected to a digital analog converter (DAC) 524. In one arrangement, DAC 524 may be provided to interface with appropriate floating voltage supply (e.g., having suitable magnitude and polarity, depending on the type of stimulation current being programmed) to generate a digitally-programmed analog voltage level as an output signal coupled to the first terminal of the error amplifier 522. As illustrated, the error amplifier 522 may be implemented as an op amp having two inputs for providing a differential input and operative with the pair of power supply rail voltage nodes 530, 528. In some arrangements, nodes 530, 528 may be selectively biased depending on whether cathodic stimulation current or anodic stimulation current is being programmed. Regardless of whether anodic or cathodic stimulation is programmed, the digitally-programmed analog voltage signal output (VDAC) from DAC 524 may be coupled to the first input of the error amplifier 522 as noted above, wherein the second input is coupled to a programmable resistor network 532 operative to provide a digitally-programmed resistance (RSCALE) 532 in a feedback loop arrangement 531 for modulating or otherwise adjusting a stimulation current output. In operation, the error amplifier 522 may be programmatically configured to generate a desired amount of stimulation current ($I_{STIM}$), which may be set by the application of Ohm's Law in view of the digitally-programmed resistance RSCALE, where $I_{STIM}$=(VDAC/RSCALE), at a node 537 to which the programmable resistor network 532 is connected. The VDAC output of DAC 524 may be controlled by the pulse generator circuitry to output a reference voltage that defines a stimulation profile of the stimulation therapy. Feedback loop path 531 coupled to the second input (negative) input of the error amplifier 522 is operative to provide a feedback signal indicative of the current pulled from the active electrode E3 506-3 via a current conducting device 535 (e.g., a MOSFET). The CR circuit 520 generates an output current based on the voltage across the variable RSCALE resistor network 532, which is controlled by the voltages at the first and second input terminals (positive and negative terminals) corresponding to the feedback signal 531 and the VDAC reference voltage from DAC 524. The output of the error amplifier 522 is connected to, and drives, a gate of the current conducting device 535, wherein a drain thereof is connected to E3 506-3 and a source thereof is connected to the variable RSCALE network 532 at the feedback node 537. In essence, the current conducting device 535 is configured to regulate the stimulation current flow ($I_{STIM}$, also referred to as $I_{TISSUE}$) sourced from E2 506-2 through the patent's tissue to E3 506-3 based on the control voltage signal output by the error amplifier 522.

During delivery of stimulation, the anodic electrode E2 506-2 and the cathodic electrode E3 506-3 are energized such that voltages $V_{ANODE}$ and $V_{CATHODE}$ developed thereat provide a stimulation current $I_{STIM}$ flowing through at least portion of the ETI network 504 that represents the target tissue. As E2 506-2 is driven by a voltage multiplier (VM) 533, the voltage $V_{ANODE}$ corresponds to the voltage across voltage multiplier 534 that is coupled to the floating ground 528. While not specifically illustrated in this FIG., it is understood that VM 533 may be implemented as a charge pump having a capacitor bank that may be connected to the IPG battery through a suitable switching arrangement. Accordingly, VM 533 may be charged by the IPG battery to a desired voltage level and then disconnected from the battery (and disconnected from a fixed ground) to allow VM 533 to function as a floating voltage multiplier, wherein a voltage level at the negative terminal fluctuates up and down with the voltage level at the floating ground node 528. In the example circuit arrangement 500 of FIG. 5, VM 533, DAC 524, error amplifier 522, charge pump 526 and RSCALE resistor network 532 are therefore all connected to the floating ground node 528 and thus are allowed to drift up and down by a similar amount as a voltage at the floating ground node 528 may fluctuate relative to a fixed reference ground 551 (e.g., corresponding to the negative terminal of the battery) in order to maintain a stimulation profile even while experiencing an EMI event. When in the presence of an EMI event, the voltage at the floating ground node 528 is allowed to drift upward and/or downward in response to the induced interference, and based thereon voltages may drift upward and/or downward by related amounts at $V_{ANODE}$ and $V_{CATHODE}$ terminals driving electrodes E2 and E3, respectively, as well as the power supply terminals of the error amplifier 522 (nodes 530, 528), feedback path 531 and feedback node 537. By allowing the floating ground node 528 to drift upward and/or downward, such as when exposed to EMI interference, a practice of example embodiments herein affords sufficient operating range or headroom to avoid voltage "clamping" by the charge pump 526, error amplifier 522, DAC 524, Zener protection diodes 540-1 to 540-3, Zener protection diodes 542-1 and 542-2, voltage multiplier 533 and/or other components. Accordingly, all such components may be advantageously prevented from reaching or exceeding an outer voltage of the normal operating range of such components and/or from entering a clamping state.

In the example circuit arrangement 500 of FIG. 5, EMI interference voltages may be modeled as interference sources 512-1 to 512-3 at respective electrodes 506-1 to 506-3 that may be developed or induced during an EMI event (e.g., such as during an MRI scan). An interference source 512-1 is modeled as a voltage source that is introduced at the inactive electrode E1 506-1 when the inactive electrode E1 is exposed to EMI interference. Interference sources 512-2 and 512-3 are similarly modeled as voltage sources that are introduced at the active electrodes E2 and E3 when the active electrodes E2 and E3 are exposed to EMI. The magnitude of the voltage introduced by the interference sources 512-1 to 512-3 may fluctuate over time in a substantially similar manner (although not necessarily identically) at the active and inactive electrodes E1-E3, as previously noted.

In one representation of the ETI network 504, each electrode is shown as exhibiting certain similar capacitive and resistive characteristics while implanted in the patient tissue that may be modeled in a simplified manner as set forth previously. The active anodic electrode E2 506-2 exhibits a bulk resistance 510-2 coupled in series with capacitor 508-2 (e.g., having a 3 µF capacitance) that represents a combination of the $C_{DC}$ and $C_{DL}$ capacitances associated with E2 506-2. The active cathodic electrode E3 506-3 exhibits a bulk resistance 510-3 coupled in series with capacitor 508-3 (e.g., having a 3 µF capacitance) that represents a combination of the $C_{DC}$ and $C_{DL}$ capacitances associated with E3 506-3. Likewise, the inactive Kelvin connect electrode E1 506-1 (operating as an EMI antenna) exhibits a resistance 510-1 coupled in series with capacitor 508-1 (e.g., having a 3 µF capacitance) representing a combination of the $C_{DC}$ and $C_{DL}$ capacitances associated therewith. Generally, electrodes E1-E3 may be designed to have similar capacitive and resistive characteristics, such that the respective resistances are substantially similar and the respective capacitances are substantially similar. Optionally, when a "dummy" wire is used as the EMI antenna, the wire may also be configured to have substantially similar capacitive, resistive, and interference voltage characteristics as the active electrodes E2, E3. While a separate dummy wire is not illustrated in FIG. 5, it is understood that the wire EMI antenna would preferably be connected to the circuit arrangement 500 of FIG. 5 at the Case node 509 (rather than a COMMON node 511, where electrodes E1-E3 connect to the human tissue), since the non-electrode dummy wire must not electrically conduct to human tissue. During stimulation, a stimulation current ($I_{STIM}$ or $I_{TISSUE}$) is delivered between E2 and E3 in the direction indicated by the arrows illustrated relative to the ETI arrangement 504 of FIG. 5. On the other hand, substantially no current flows in the Kelvin connect node path or the COMMON node path which couples Case node 509 associated with the IPG to the COMMON node 511 via suitable capacitive and resistive components, e.g., resistor 515 coupled to capacitor 513 (e.g., having a capacitance of 22 µF).

In one arrangement, Case node 509 is driven by the charge pump voltage source 550 that may be generated from the battery of the IPG and is configured to maintain a common-mode voltage reference $V_{COM}$ at the Case node 509, thereby maintaining a predetermined average voltage potential across the entire electrode network. The voltage source 550 includes a negative terminal that is connected to the negative terminal of the battery at the ground 551. Capacitor 513 is operative as a DC blocking capacitor configured to prevent DC current flow through the Case.

In one example embodiment, the circuit arrangement 500 of FIG. 5 may also include suitable Zener diode protection circuitry with respect to each electrode as well as the Case node. By way of illustration, diodes 540-1 to 540-3 are connected to the corresponding electrodes E1-E3 and diodes 542-1 and 542-2 are associated with Case node 509, which provide electrical damage protection to the biostimulation system from electrostatic discharge (ESD) and/or cardiac defibrillation. More specifically, diode 540-1 is disposed between E1 506-1 and a floating voltage (VFLOAT); diode 540-2 is disposed between E2 506-2 and VFLOAT; and diode 540-3 is disposed between E3 506-3 and VFLOAT. Diodes 542-1 and 542-2 are connected in a back-to-back anode arrangement between the Case node 509, the negative battery terminal 551, wherein the floating voltage (VFLOAT) is commonly provided to drive the anode terminals of diodes 542-1 and 542-2. Skilled artisans will recognize that floating voltages that can vary in both positive and negative directions may preferably be provided to drive the Zener diodes so that proper Zener protection is afforded to the electrodes for both positive and negative voltage swings. Additional details regarding an enhanced Zener protection scheme for an IPG may be found in U.S. patent application Ser. No. 16/433,975, filed Jun. 6, 2019, entitled, "SYSTEMS AND METHODS FOR IMPROVED DAMAGE PROTECTION DURING ELECTROSTATIC DISCHARGE AND CARDIAC DEFIBRILLATION, AND FOR SUBSTANTIALLY IMPROVED STIMULATION INTERFERENCE MITIGATION IN IMPLANTABLE PULSE GENERATORS", which is incorporated by reference herein.

In accordance with the teachings of the present patent disclosure, a diagnostic circuit 502 comprising a tandem pair of comparators 597, 599 is provided for monitoring and counteracting an interference voltage ($V_{IF}$) from MRI/EMI induced upon the Kelvin connect electrode E1 506-1 of the IPG. In one embodiment, comparators 599, 597 are configured to generate digital control signals, $V_{COM\_UP}$ 561 and $V_{COM\_DOWN}$ 563, respectively, which can be used to increase or decrease the output of charge pump voltage source 550 operative to supply a common-mode voltage reference for the IPG circuitry as discussed above. More specifically, comparators 599, 597, or other suitable logic circuitry, may be operative based on measuring or otherwise monitoring that the amount of interference voltage on the Kelvin connect electrode E1 506-1 is different than the common-mode voltage reference $V_{COM}$ by a particular margin or threshold. As $V_{COM}$ charge pump voltage source 550 is not used in delivering stimulation current to the electrodes, an example embodiment may involve a very low power charge pump operative with a single-bit digital control signal to increase or decrease the $V_{COM}$ set point such that the target voltage output is incremented or decremented in a single voltage step. Accordingly, by comparing a difference between $V_{IF}$ and $V_{COM}$ at any time during, before or after stimulation to a configurable and/or predetermined threshold (which can be a positive threshold or negative threshold, depending on the direction of the deviation), a determination may be made whether to reduce or increase the $V_{COM}$ output by a predetermined set amount in real time so as to incrementally and adaptively mitigate the effect of the interference voltage on the IPG.

In one arrangement, the Kelvin connect electrode E1 506-1 is commonly coupled to an inverting input of comparator 599 and to a non-inverting input of comparator 597 (which may be referred to as sense inputs), wherein a corresponding threshold reference (VCM_VREF) may be provided to the non-inverting and inverting inputs of the respective comparators 599, 597 (which may be referred to as reference inputs). Supply rails for comparators 597, 599 may be driven by power supplies that remain unaffected during an EMI event such that the logic operations associated with comparators 597, 599 continue to be valid. In one nonlimiting example scenario, if the interference voltage is different than $V_{COM}$ by ±1.0 V, either $V_{COM\_UP}$ signal 561 or $V_{COM\_DOWN}$ signal 563 may be generated to inversely track the EMI-induced voltages on the Kelvin connect electrode E1 506-1. That is, if $V_{IF} > V_{COM}$ by ±1.0 V, $V_{COM\_DOWN}$ control signal 563 comprising a 1-bit digital control signal is generated by comparator 597 (also referred to as a first comparator), which actuates $V_{COM}$ charge pump 550 to decrement its common-mode voltage reference output by a set amount. Likewise, if $V_{IF} < V_{COM}$ by −1.0 V, VCOM_UP control signal 561 comprising a 1-bit digital control signal is generated by comparator 599 (also referred to as a second comparator), which causes $V_{COM}$ charge pump 550 to increment its common-mode voltage reference output by a set amount. In one arrangement, the 1-bit digital control signals 561, 563 are operative to cause a counter disposed in the $V_{COM}$ charge pump 550 to change its N-bit control setting by a single bit so as to generate an increment or decrement step in the output voltage. Additional details regarding an example charge pump implementation that may be configured to operate under suitable digital control as one or more charge pumps and/or voltage multipliers of the circuit arrangement 500 may be found in U.S. Pat. No. 8,446,212, entitled "PULSE GENERATOR HAVING AN EFFICIENT FRACTIONAL VOLTAGE CONVERTER AND METHOD OF USE", which is incorporated herein by reference. An example embodiment may therefore be configured such that $V_{COM}$ output generated by the charge pump source 550 can be adaptively and preferably continuously maintained to bias the IPG circuitry for optimal operating headroom and to inversely adjust its voltage output based on the induced voltages on the stimulation leads for counterbalancing the effects thereof in real time.

As a nonlimiting example, assume during an EMI event that the $V_{COM}$ common-mode voltage reference 550 is maintained between ±10 V. When no EMI interference is present, the voltages at $V_{COM}$ and at the floating ground node 528 may be biased to approximately 0 V. When EMI interference is experienced in a conventional IPG/IMD system, the EMI interference adds voltage interferences at the electrodes E2 and E3 that cause their voltages to fluctuate upward and downward (e.g., in a sinusoidal manner). The voltage interferences at electrodes E2 and E3 would also cause the voltage at the floating ground node 528 to similarly fluctuate upward and downward by an amount substantially corresponding to the voltage interference, if the $V_{COM}$ voltage were held at a constant value. However, in a biostimulation system formed in accordance with embodiments herein, the $V_{COM}$ common-mode voltage reference 550 can be adjusted in real time to substantially cancel out the voltage interference caused by EMI in an incremental manner. Such interference mitigation behavior will hold the unused electrode E1 and the active electrodes E2 and E3 substantially constant at the average $V_{COM}$ voltage, which will prevent voltage excursions for other electrical nodes in the IPG/IMD system from causing deleterious effects while maintaining safe and effective stimulation therapy for the patient during the presence of EMI.

It should be appreciated that in the foregoing interference mitigation control mechanism, the $V_{COM}$ voltage can be adjusted in real time (even while stimulation is being delivered) for counterbalancing the induced interference voltages on the stimulation lead wires even for interference signals as large as ±10 V to ±11 V voltages induced on SCS leads by an MRI gradient field. Further, such $V_{COM}$ control action is helpful in preventing the parasitic diodes of the stimulation circuitry (e.g., diodes in the CR circuit and electrode switches) as well as the IPG protection circuitry (e.g., Zener diodes) from forward biasing, thereby preventing unintended stimulation currents from flowing through the patient when no stimulation is intended.

Skilled artisans will recognize upon reference hereto that although a particular type of tandem comparator arrangement is illustrated in FIG. 5, diagnostic circuitry 502 may also be implemented using various other combinations of electronic devices and components, such as, e.g., differential op amps, voltage measurement monitors, differential threshold reference sources, state machines, processors, etc., in order to practice an embodiment of the EMI mitigation scheme according to the teachings disclosed herein.

Turning to FIGS. 3A-3C, depicted therein are flowcharts illustrative of blocks, steps and/or acts that may be (re)combined or (re)organized in one or more arrangements with or without other flowcharts for monitoring and mitigating induced interference voltages according to some embodiments of the present disclosure. Process 300A shown in FIG. 3A sets forth an overall EMI mitigation scheme for an IPG/IMD system according to an example embodiment. At block 302, a plurality of electrodes of the IMG's implantable lead system may be configured as having at least one active electrode and at least one inactive electrode. At block 304, a charge pump voltage source is provided and configured to output a common-mode voltage reference with respect to one or more circuitry portions of the pulse generator configured to energize one or more electrodes. At block 306, an interference voltage induced at an inactive electrode, an unused sense terminal, or an EMI antenna (e.g., operating as a Kelvin connection node) is measured, compared, detected or otherwise monitored by using suitable diagnostic circuitry. At block 308, one or more control signals may be generated by the diagnostic circuitry to adjust the common-mode voltage reference output by the charge pump voltage source, e.g., depending on a difference between the induced voltage sensed at the Kelvin connection node and the common mode voltage reference, wherein such difference is determined or monitored in real time and the common-mode reference voltage adjustment is made accordingly. In one embodiment, the EMI mitigation scheme may involve generating at least a first control signal responsive to determining that the induced interference voltage is greater than the common-mode voltage reference is by a first threshold, the first control signal operative to decrease the common-mode voltage reference output of the charge pump voltage source by a predetermined amount, as set forth at block 322 of process 300B shown in FIG. 3B. As noted previously, the first control signal may comprise a 1-bit digital control signal. In one embodiment, the EMI mitigation scheme may involve generating at least a second control signal responsive to determining that the induced interference voltage is less than the common-mode voltage reference by a second threshold, the second control signal operative to increase the common-mode voltage reference output of the charge pump voltage source by a predetermined amount, as set forth at block 332 of process 300C shown in FIG. 3C, wherein the second control signal may comprise a 1-bit digital control signal.

FIGS. 4A-4C depict additional blocks, steps and/or acts that may be (re)combined in one or more arrangements with or without other flowcharts of the present disclosure according to some additional embodiments. At block 402 of example process 400A shown in FIG. 4A, an embodiment may comprise setting a Kelvin connection selection mode to configure one or more electrodes and/or EMI antenna for effectuating appropriate connections to the diagnostic circuitry comparators. As noted previously, a compete ETI representation of an implantable lead system may include $C_{SENSE}$ terminals, $C_{DC}$ terminals, and/or one or more designated EMI antenna traces, wherein any number of unused $C_{SENSE}$ terminals, electrodes unused for stimulation, and/or EMI antenna traces may be configured as Kelvin connection nodes based on a selection scheme such that different permutations and combinations of measurement connection paths may be established with the diagnostic circuitry comparators for purposes of sensing induced voltages due to an EMI event. In some embodiments, therefore, at least one inactive electrode may be configured as a dedicated Kelvin connect electrode of the implantable lead system for facilitating at least one Kelvin connection path for measuring and monitoring induced interference voltage, as set forth at block 412 of process 400B shown in FIG. 4B. Further, at least one active electrode may be configured as one of a cathode to provide cathodic stimulation or an anode to provide anodic stimulation to a patient's tissue according to a particular therapy application, as set forth at block 422 of example process 400D of FIG. 4D. As is known in the art, such therapy applications may comprise a therapy selected from at least one of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a cardiac pacemaker therapy, a cardioverter-defibrillator therapy, a cardiac rhythm management (CRM) therapy, an electrophysiology (EP) mapping and radio frequency ($R_F$) ablation therapy, an electroconvulsive therapy (ECT), a repetitive transcranial magnetic stimulation (rTMS) therapy, and a vagal nerve stimulation (VNS) therapy.

Figure 6:
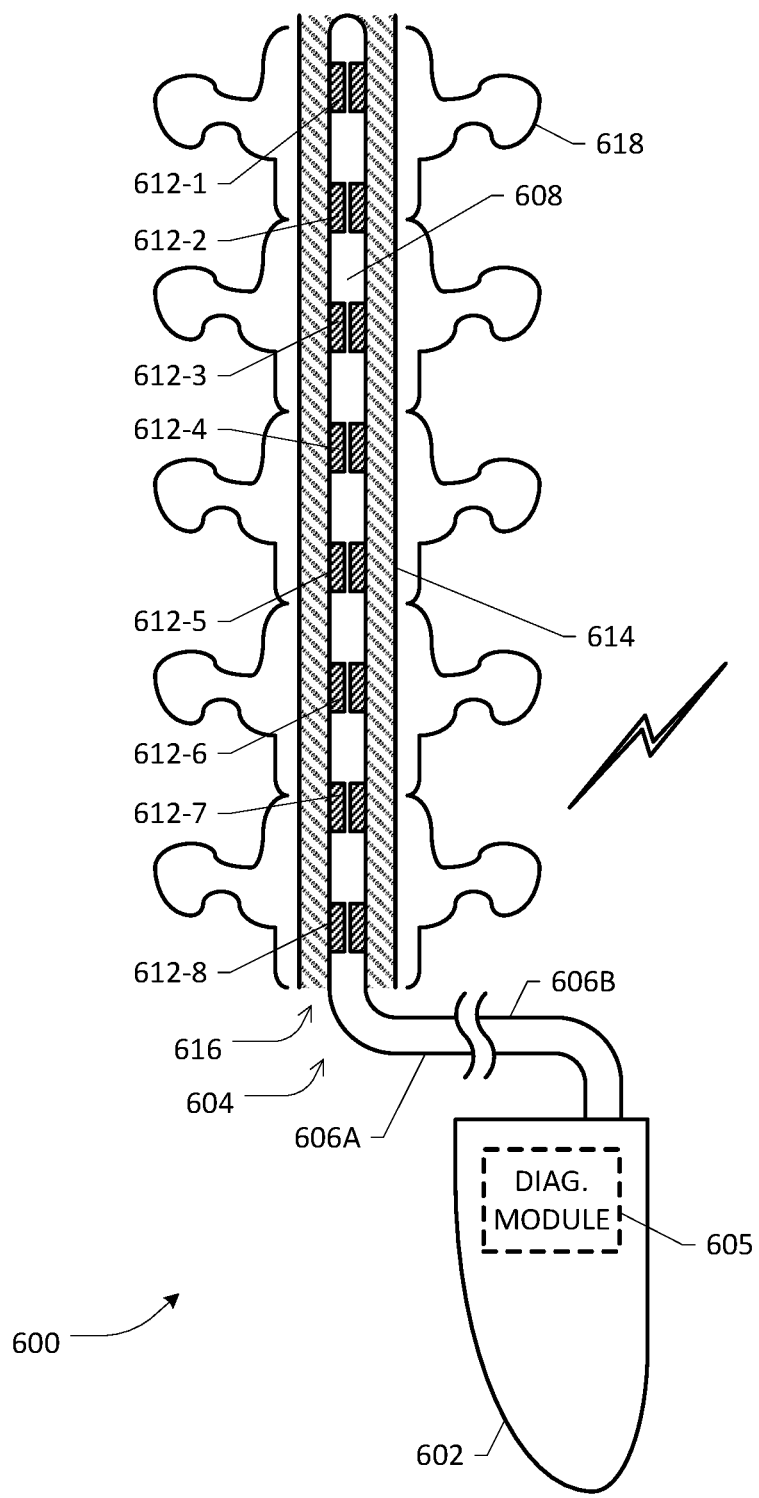
FIG. 6 illustrates an example spinal cord stimulation (SCS) therapy application involving an IPG/IMD and associated lead system having a plurality of electrodes wherein an induced interference voltage may be monitored and mitigated according to an embodiment of the present disclosure.

FIG. 6 depicts an example spinal cord stimulation (SCS) therapy application 600 involving an IPG/IMD 602 and associated lead system 604 having a plurality of electrodes 612-1 to 612-8 wherein an induced voltage due to an EMI event may be monitored and mitigated using an embodiment of the present disclosure. Preferably, the lead system 604 comprises a lead body 606A/B coupled to an implantable lead 608 that may be positioned at a desired target position in an epidural space 616 defined by a plurality of vertebrae 618 of a patient so as to be in close proximity to a nerve tissue of interest, e.g., a spinal cord 614. Example lead 608 includes eight electrodes 612-1 to 612-8, which may comprise ring electrodes, segmented or split electrodes, etc. that may be separated from one another by equal or unequal portions of encapsulating material. The implantable lead 608 is connected via lead body 606A/506B to the pulse generator or IMD 602 that includes at least an embodiment of a Kelvin connection scheme configured to be operative with suitable diagnostic circuitry 605 of the present disclosure. At least a subset of the electrodes 612-1 to 612-8 may be selectively energized, i.e., stimulated to a target setting, according to a therapy program. As an EMI event is encountered, induced voltage measurements may be taken by effectuating a switchable combination of Kelvin connections with respect to the electrodes in connection with the diagnostic circuitry 605. For example, in one embodiment electrodes 612-1, 612-4 and 612-8 may be programmed as cathodes or anodes for operation in conjunction with the case or can of the IPG/IMD 602 for providing current stimulation to effectuate an electric field that is spatially distributed over a target portion of the spinal cord 614. An unused electrode, e.g., electrode 612-5, may be used to establish a Kevin connect electrode path to the diagnostic circuitry 605, wherein the interference voltage induced at the electrode 612-5 may be measured/monitored for generating suitable 1-bit digital control signals to counterbalance the effect of the induced voltage by adjusting a common-mode voltage reference used in the IPG circuitry.

Although a single implantable lead 608 is exemplified in FIG. 6, it should be appreciated that a lead system comprising multiple leads, each having a corresponding plurality of electrodes, may be implemented in a stimulation therapy application, wherein appropriate Kelvin connect electrode paths may be established for different subsets of active and unused electrodes of the lead system.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or nonvolatile memories such as, e.g., random access memory (RAM), electrically erasable/programmable read-only memories (EEPROMs) or UV-EPROMS, one-time programmable (OTP) memories, Flash memories, static RAM (SRAM), etc.

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Where the phrases such as "at least one of A and B" or phrases of similar import are recited or described, such a phrase should be understood to mean "only A, only B, or both A and B." Reference to an element in the singular is not intended to mean "one and only one" unless explicitly so stated, but rather "one or more." Moreover, the terms "first," "second," and "third," etc. employed in reference to elements or features are used merely as labels, and are not intended to impose numerical requirements, sequential ordering or relative degree of significance or importance on their objects. All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. A method of mitigating electromagnetic interference (EMI) in an implantable medical device (IMO) having a pulse generator configured to supply stimulation to tissue of a patient, the method comprising:
    monitoring an interference voltage sensed at a Kelvin connection node associated with an implantable lead system of the IMO; and
    generating one or more control signals to adjust a common-mode voltage reference output by a charge pump voltage source of the IMO depending on a difference between the common-mode voltage reference and the interference voltage sensed at the Kelvin connection node, wherein the one or more control signals comprise at least a first control signal generated responsive to determining that the interference voltage is greater than the common-mode voltage reference by a first threshold, the first control signal comprising a control signal operative to decrease the common-mode voltage reference output of the charge pump voltage source.

2. The method as recited in claim 1, wherein the one or more control signals comprise at least a second control signal generated responsive to determining that the interference voltage is less than the common-mode voltage reference by a second threshold, the second control signal operative to increase the common-mode voltage reference output of the charge pump voltage source.

3. The method as recited in claim 2, wherein the first control signal and the second control signal comprise 1-bit digital control signals.

4. The method as recited in claim 2, wherein the first and second thresholds are a same value.

5. The method as recited in claim 2, wherein the interference voltage is induced due to least one of a magnetic resonance imaging (MRI) of the patient and an electromagnetic interference (EMI) event encountered by the patient.

6. The method as recited in claim 2, further comprising configuring at least one active electrode of the implantable lead system as one of a cathode to provide cathodic stimulation to the patient's tissue and an anode to provide anodic stimulation to the patient's tissue with respect to a particular therapy application.

7. The method as recited in claim 6, wherein the particular therapy application comprises a therapy selected from at least one of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a drug delivery therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial magnetic stimulation (rTMS) therapy, and a vagal nerve stimulation (VNS) therapy.

8. The method as recited in claim 2, further comprising configuring at least one of an inactive electrode of the implantable lead system, an unused sense capacitor terminal of an active electrode of the implantable lead system and an EMI antenna as the Kelvin connection node.

* * * * *

UNITED STATES PATENT AND TRADEMARK OFFICE
CERTIFICATE OF CORRECTION

PATENT NO. : 12,144,984 B2  
APPLICATION NO. : 16/931030  
DATED : November 19, 2024  
INVENTOR(S) : Steven Boor et al.

Page 1 of 1

It is certified that error appears in the above-identified patent and that said Letters Patent is hereby corrected as shown below:

In the Specification

At Column 16, Line number 67, delete "VB" and replace with --$V_B$--.
At Column 20, Line number 60, delete "$V_{COM\_UP}$" and replace with --VCOM_UP--.
At Column 20, Line number 61, delete "$V_{COM\_DOWN}$" and replace with --VCOM_DOWN--.
At Column 21, Line number 30, delete "$V_{COM\_UP}$" and replace with --VCOM_UP--.
At Column 21, Line number 31, delete "$V_{COM\_DOWN}$" and replace with --VCOM_DOWN--.
At Column 21, Line number 34, delete "$V_{COM\_DOWN}$" and replace with --VCOM_DOWN--.
At Column 23, Line number 57, delete "($R_F$)" and replace with --(RF)--.

Signed and Sealed this  
Thirty-first Day of December, 2024

Derrick Brent  
*Acting Director of the United States Patent and Trademark Office*